United States Patent [19]

Beaudet et al.

[11] Patent Number: 5,602,307

[45] Date of Patent: Feb. 11, 1997

[54] NON-HUMAN ANIMAL HAVING PREDEFINED ALLELE OF A CELLULAR ADHESION GENE

[75] Inventors: Arthur L. Beaudet, Houston, Tex.; Raymond Wilson, Timonium, Md.; Allan Bradley, Houston, Tex.; William E. O'Brien, Houston, Tex.; James Sligh, Houston, Tex.; Christie Ballantyne, Houston, Tex.; Daniel Bullard, Houston, Tex.

[73] Assignee: Baylor College of Medicine, Houston, Tex.

[21] Appl. No.: 309,549

[22] Filed: Sep. 20, 1994

Related U.S. Application Data

[63] Continuation of Ser. No. 928,010, Aug. 12, 1992, abandoned.

[51] Int. Cl.$^6$ .................. C12N 15/00; C12N 5/00; A61K 49/00
[52] U.S. Cl. .................. 800/2; 800/DIG. 1; 424/9.2; 424/9.1; 435/172.3; 935/62
[58] Field of Search .................. 800/2, DIG. 1; 435/172.3, 240.2; 424/9.1, 9.2; 935/62, 111

[56] References Cited

U.S. PATENT DOCUMENTS

| | | | |
|---|---|---|---|
| 4,736,866 | 4/1988 | Leder et al. | 800/1 |
| 4,870,009 | 9/1989 | Evans et al. | 435/70 |

FOREIGN PATENT DOCUMENTS

| | | |
|---|---|---|
| 289949 | 11/1988 | European Pat. Off. ........ C12N 15/00 |
| WO82/04443 | 12/1982 | WIPO. |
| WO87/05325 | 9/1987 | WIPO. |
| WO87/07298 | 12/1987 | WIPO. |

OTHER PUBLICATIONS

Wilson et al. (a), J. Cell Biochem. Suppl. O (16 Part A), p. 58 (1992).
Wilson et al. (b), Biophys. J. 61 (2 Part 2): A413 (1992).
Wilson et al. (c), Clin. Res. 40(2): 339A (1992).
Wilson et al. (d), Clin. Res. 39(2): 337A (1991).
Mansour, GATA 7(8): 219–227 (1990).
Robertson, Biology of Reproduction 44: 238–245 (1991).
Sanders et al., Blood 80(3): 795–800 (1992).
Wilson et al. (e), Nucleic Acids Res. 17(13): 5397 (1989).
Ballantyne et al. (a), Clin. Res. 39(2): 337A (1991).
Ballantyne et al. (b), Nucleic Acids Res. 17(14): 5853 (1989).
Sligh et al., J. Cell Biochem Suppl. O (16 Part A): 58 (1992).
Springer, T. A. et al., Fed. Proc. 44:2660–2663 (1985).
Anderson, D. C. et al., Ann Rev. Med. 38:175–194 (1987).
Staunton, D. E. et al., Cell 61:243–254 (1990).
de Fougerolles, A. R. et al., J. Exper. Med. 174:253–267 (1991).
Gallatin, W. M. et al., Nature 304:30–34 (1983).
Tedder, T. F. et al., J. Exper. Med. 170:123–133 (1989).
Larson, R. S. et al., Immunol. Rev. 114:181–217 (1990).
Springer, T. A., Nature 346:425–434 (1990).
Hemler, M. E. et al., Immunol. Rev. 114:45–65 (1990).
Palmiter, R. D. et al., Science 222:809–814 (1983).
Stewart, T. A. et al., Science 217:1046–1048 (1982).
Jaenisch, R., Science 240:1468–1474 (1988).
Gossler, A. et al., Proc. Natl. Acad. Sci. (U.S.A.) 83:9065–9069 (1986).
Wagner, E. F. et al., Cold Spring Harb. Symp. Quant. Biol. 50:691–700 (1985).
Brinster, R. L. et al., Proc. Natl. Acad. Sci. (U.S.A.) 86:7087–7091 (1989).
Capecchi, M. R., Trends Genet. 5:70–76 (1989).
Capecchi, M. R. Science 244:1288–1292 (1989).
Doetschman, T. et al., Proc Natl. Acad. Sci. (U.S.A.) 85:8583–8587 (1988).
Evans, M. J. et al., Nature 292:154–156 (1981).
Evans, M. J. et al., Cold Spring Harb. Symp. Quant. Biol. 50:685–689 (1985).
Frohman, M. A. et al., Cell 56:145–147 (1989).
Thompson, S. et al., Cell 56:313–321 (1989).
Smithies, O. et al., Nature 317:230–234 (1985).
Schwartzberg, P. L. et al., Science 246:799–803 (1989).
Thomas, K. R. et al., Cell 51:503–512 (1987).
Mansour, S. L. et al., Nature 336:348–352 (1988).
Koller, B. H. et al., Proc. Natl. Acad. Sci. (U.S.A.) 86:8932–8935 (1989).
Koller, B. H. et al., Proc. Natl. Acad. Sci. (U.S.A.) 86:8927–8931 (1989).
Sedivy, J. M., Bio–Technol. 6:1192–1196 (1988).
Bradley, A. (In: Teratocarcinomas and Embryonic Stem Cells: A Practical Approach, (E. J. Robertson, Ed.), IRL Press, Oxford, 1987, pp. 113–151).
Bradley, A. et al., Curr. Top. Devel. Biol. 20:357–371 (1986).
Boggs, S. S., Int. J. Cell Clon. 8:80–96 (1990).
Zijlstra, M. et al., Nature 342:435–438 (1989).
Zijlstra, M. et al., Nature 344:722–746 (1989).
Gough, N. M. et al., Reprod. Fertil. Dev. 1:281–288 (1989).
Gridley, T. et al., Trends Genet. 3:162 (1987).

Primary Examiner—Jasemine C. Chambers
Attorney, Agent, or Firm—Fulbright & Jaworski L.L.P.

[57] ABSTRACT

A transgenic mouse which contains a predefined, specific and desired alteration in at least one of its two chromosomal alleles of a cellular adhesion gene, such that at least one of these alleles contains a mutation which alters the expression of the allele.

12 Claims, 9 Drawing Sheets

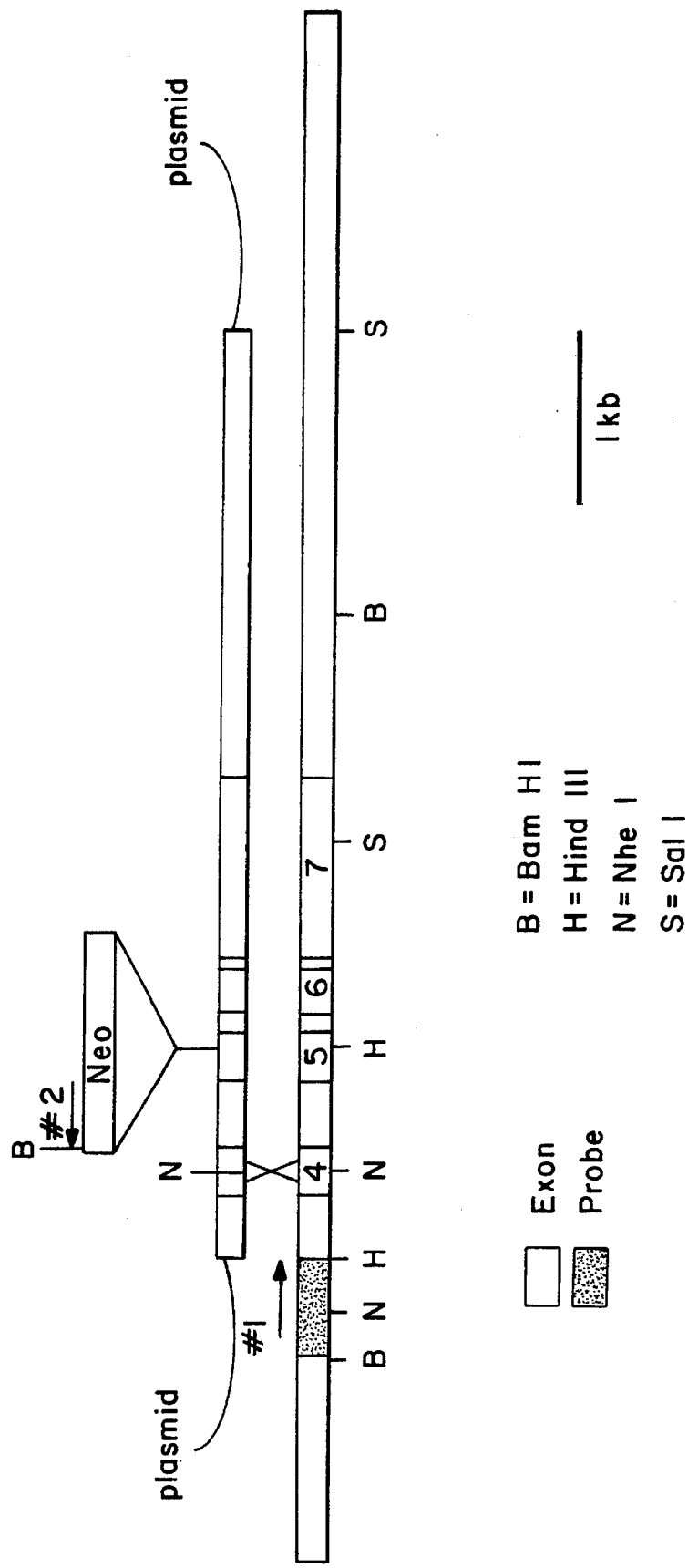

P-selectin replacement vector

P-selectin genomic DNA

Mutated P-selectin locus

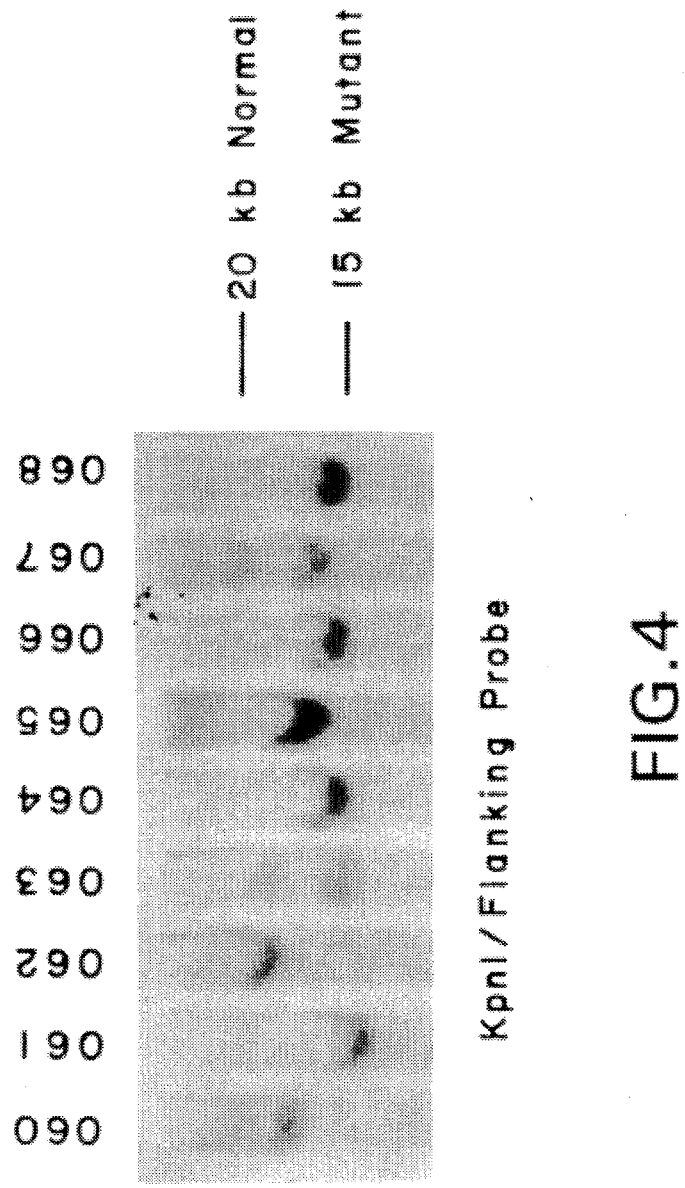

NON-HUMAN ANIMAL HAVING PREDEFINED ALLELE OF A CELLULAR ADHESION GENE

This application is a continuation of U.S. application Ser. No. 07/928,010, filed Aug. 12, 1992, now abandoned.

FIELD OF THE INVENTION

The invention is directed toward non-human transgenic or chimeric animals that carry predefined alleles in any of a set of genes that are responsible for mediating leukocyte-endothelial cell adhesion. The invention further pertains to the use of such animals in the development of agents and therapies for the treatment of inflammation and other diseases and conditions. This invention was funded in part with Government funds (NIH Grants AI32177 and AR01813). The Government has certain rights in this invention.

BACKGROUND OF THE INVENTION

I. CELLULAR ADHESION

In order to properly defend a host against foreign invaders such as bacteria or viruses, leukocytes must be able to migrate from the circulation to sites of infection and inflammation. Leukocytes must also be able to attach to antigen-presenting cells so that a normal specific immune response can occur, and finally, they must attach to appropriate target cells so that lysis of virally-infected or tumor cells can occur. Each of these migration processes requires that leukocytes have the ability to adhere to other cells, especially endothelial cells. An excellent review of the properties and characteristics of leukocytes is provided by Eisen, H. W., (*In: Microbiology,* 3rd Ed., Harper & Row, Philadelphia, Pa. (1980), pp. 290–295 and 381–418).

Three classes of molecules have been found to have a role in mediating cellular adhesion: molecules of the integrin family, molecules of the super-immunoglobulin family, and molecules of the selectin family.

A. THE ADHESION MOLECULES OF THE INTEGRIN FAMILY

The receptor molecules of the integrin family that are involved in cellular adhesion have been termed the "CD11/CD18 family of receptor molecules." These molecules were originally identified using hybridoma technology (Davignon, D. et al., *Proc. Natl. Acad. Sci. USA* 78:4535–4539 (1981); Springer, T. et al. *Eur. J. Immunol.* 9:301–306 (1979); Springer, T. et al., *Fed. Proc.* 44:2660–2663 (1985)).

The receptor molecules of the CD11/CD18 family are heterodimers containing an α subunit (CD11) and a β subunit (CD18) (Sanchez-Madrid, F. et al., *J. Exper. Med,* 158:1785–1803 (1983); Keizer, G. D. et al., *Eur. J. Immunol.* 15:1142–1147 (1985)). The β chain of the three molecules is identical. Although the α chains of the heterodimers differ, close analysis has revealed that there are substantial similarities between them. Reviews of the similarities between the α subunits of the LFA-1 related glycoproteins are provided by Sanchez-Madrid, F. et al., (*J. Exper. Med.* 158:586–602 (1983); *J. Exper. Med.* 158:1785–1803 (1983)).

The three different α subunits have been termed: CD11a (equivalently referred to as the LFA-1 α subunit), CD11b (equivalently referred to as the Mac-1 α subunit) and CD11c (equivalently referred to as the p150,95 α subunit) (E. Ruoslahti et al., *Science* 238:491 (1987); D. C. Anderson et al., *Ann. Rev. Med.* 38:175 (1987)).

The CD18 molecules were found to have a molecular weight of 95 kd whereas the molecular weights of the α chains were found to vary from 150 kd to 180 kd (Springer, T., *Fed. Proc.* 44:2660–2663 (1985)).

The CD11a/CD18 heterodimer is found on most lymphocytes (Springer, T. A., et al. *Immunol. Rev.* 68:111–135 (1982); E. Ruoslahti et al., *Science* 238:491 (1987); D. C. Anderson et al., *Ann. Rev. Med.* 38:175 (1987)). The CD11b/CD18 and CD11c/CD18 heterodimers are found on macrophages, granulocytes and large granular lymphocytes (Ruoslahti et al., *Science* 238:491 (1987); D. C. Anderson et al., *Ann. Rev. Med.* 38:175 (1987)). These three molecules play a role in cellular adhesion (Keizer, G. et al., *Eur. J. Immunol.* 15:1142–1147 (1985)).

The importance of the CD11a/CD18 complex and its cellular ligands in host defense has been illuminated by identification of an autosomal recessive trait (designated "LAD" Syndrome for Leukocyte Adhesion Deficiency Syndrome) characterized by recurrent, severe bacterial infections in which affected individuals are unable to synthesize normal CD18 molecules (E. Ruoslahti et al., *Science* 238:491 (1987); D. C. Anderson et al., *Ann, Rev. Med.* 38:175 (1987); Anderson, D. C., et al., *Fed. Proc.* 44:2671–2677 (1985); Anderson, D. C., et al., *J. Infect. Dis.* 152:668–689 (1985)). Leukocytes from these patients displayed in vitro defects similar to normal counterparts whose LFA-1 family of molecules had been antagonized by antibodies. Furthermore, these individuals were unable to mount a normal immune response due to an inability of their cells to adhere to cellular substrates (Anderson, D. C., et al., *Fed. Proc.* 44:2671–2677 (1985); Anderson, D. C., et al., *J. Infect. Dis.* 152:668–689 (1985)). These data show that immune reactions are mitigated when leukocytes are unable to adhere in a normal fashion due to the lack of functional adhesion molecules of the LFA-1 family. Leukocytes from such individuals are unresponsive to stimuli which induce leukocytes to adhere to and move across vascular endothelial cells (Smith, C. W. et al., *J. Clin. Invest.* 82:1746 (1988)).

The CD11/CD18 complex is also involved in other cell-cell interactions involved in host defence against infection, including binding and phagocytosis of iC3b-opsonized particles, a property of CD11b/CD18 on granulocytes and monocytoid cells, and $Mg^{2+}$-dependent adhesion and killing of target cells by T cells and NK cells, a property of the CD11a/CD18 heteroduplex (E. Ruoslahti et al., *Science* 238:491 (1987); D. C. Anderson et al., *Ann. Rev. Med.* 38:175 (1987)).

B. THE ADHESION MOLECULES OF THE SUPER-IMMUNOGLOBULIN FAMILY

The natural binding ligand for the CD11/CD18 receptor molecules is Intercellular Adhesion Molecule-1 ("ICAM-1" or CD54) (Rothlein et al., *J. Immunol.* 137:1270 (1986)), European Patent Application Publication No. 289,949, Simmons, D. et al., *Nature* 331:624–627 (1988); Staunton, D. E. et al., *Cell* 52:925–933 (1988); which references are incorporated herein by reference).

ICAM-1 is a member of the super-immunoglobulin family of molecules. Members of this superfamily are characterized by the presence of one or more Ig homology regions, each consisting of a disulfide-bridged loop that has a number of anti-parallel β-pleated strands arranged in two sheets. Three types of homology regions have been defined, each with a typical length and having a consensus sequence of amino acid residues located between the cysteines of the disulfide bond. (Williams, A. F. et al., *Ann. Rev. Immunol.* 6:381–405 (1988); Hunkapillar, T. et al., *Adv. Immunol.* 44:1–63 (1989)).

ICAM-1 is a cell surface glycoprotein of 97–114 kd. ICAM-1 has 5 Ig-like domains. Its structure is closely related to those of the neural cell adhesion molecule (NCAM) and the myelin-associated glycoprotein (MAG) (Simmons, D. et al., *Nature* 331:624–627 (1988); Staunton, D. E. et al., *Cell* 52.:925–933 (1988); Staunton, D. E. et al., *Cell 61243–254* (1990), herein incorporated by reference).

ICAM-1 is inducible on fibroblasts and endothelial cells in vitro by inflammatory mediators such as IL-1, gamma interferon and tumor necrosis factor in a time frame consistent with the infiltration of lymphocytes into inflammatory lesions in vivo (Dustin, M. L., et. al., *J. Immunol* 137:245–254, (1986); Pober, J. S., et al., *J. Immunol* 137:1893–1896, (1986)). ICAM-1 is expressed on non-hematopoietic cells such as vascular endothelial cells, thymic epithelial cells, other epithelial cells, and fibroblasts and on hematopoietic cells such as tissue macrophages, mitogen-stimulated T lymphocyte blasts, and germinal center B-cells and dendritic cells in tonsils, lymph nodes and Peyer's patches (Dustin, M. L., et. al., *J. Immunol* 137:245–254, (1986)). ICAM-1 is expressed on keratinocytes in benign inflammatory lesions such as allergic eczema, lichen planus, exanthema, urticaria and bullous diseases.

Thus, ICAM-1 is preferentially expressed at sites of inflammation, and is not generally expressed by quiescent cells. It functions as the cellular substrate to which lymphocytes can attach, so that the lymphocytes may migrate to sites of infection or inflammation.

ICAM-2 is a second LFA-1 ligand, distinct from ICAM-1 (Rothlein, R. et al., *J. Immunol.* 137:1270–1274 (1986); Makgoba, M. W. et al., *Eur. J. Immunol.* 18:637–640 (1988); Dustin, M. L. et al., *J. Cell. Biol.* 107:321–331 (1988); Staunton, D. M. et al., *FASEB J.* 3:a446 (1989)). Like ICAM-1, ICAM-2 is a member of the super-immunoglobulin family.

ICAM-2 is constitutively expressed on endothelial cells, and on certain interstitial cells. It is also present on a variety of T-and B-lymphoblastoid cell lines. ICAM-2 is the predominant LFA-1 ligand on unactivated endothelium. It has thus been reported to play a role in normal lymphocyte recirculation, and memory cell recruitment, and to have a role in the interaction of antigen-presenting cells (deFougerolles, A. R. et al., *J. Exper. Med.* 174:253–267 (1991)).

C. THE ADHESION MOLECULES OF THE SELECTIN FAMILY

The selectin (or LECCAM) family of adhesion molecules recognize and bind carbohydrate lectins. Three selectins have been described: L-selectin (also termed LECCAM-1, MEL-14, LAM-1, LECAM-1 or lymphocyte homing receptor); E-selectin (also known as endothelial leukocyte adhesion molecule-1 (ELAM-1), or LECCAM-2); and P-selectin (also known as CD62, platelet activation dependent granule external membrane (PADGEM), LECCAM-3, or granule membrane protein-140 (GMP-140)).

L-selectin is expressed by leukocytes, and plays a role in the homing of leukocytes to peripheral lymph nodes (Gallatin, M. W. et al., *Nature* 304:30–34 (1989); Lasky, L. A. et al., *Cell* 56:1045–1055 (1989); Siegelman, M. H. et al., *Proc. Natl. Acad. Sci.* (*U.S.A.*) 86:5562–5566 (1989); Tedder, T. F. et al., J. Exper. Med. 170:123–133 (1989)). It is also expressed on granulocytes.

E-selectin is expressed on endothelial cells in response to cellular stimulation by cytokines such as TNF-α or IL-1β, or by bacterial endotoxin (LPS) (Bevilacqua, M. P. et al., *Science* 243:1160–1165 (1989); Tedder, T. F. et al., *J. Exper. Med.* 170:123–133 (1989); Bevilacqua, M. P. et al., *Proc. Natl. Acad. Sci.* (*U.S.A.*) 84:9238–9242 (1987); Luscinskas, F. W. et al., *J. Immunol.* 143:3318–3324 (1989)). In vitro, E-selectin mediates the adhesion of neutrophils, monocytes, eosinophils, a subset of lymphocytes, and certain carcinoma cells. The binding ligand of E-selectin is SLE$^x$ (Lowe, J. B. et. al., *Cell* 63:475–484 (1990)). E-selectin is expressed in chronic inflammatory disease such as rheumatoid arthritis.

P-selectin is expressed on platelets and on endothelial cells, neutrophils, other myeloid cells, and a subset of T lymphocytes (Siegelman, M. H., *Curr. Biol.* 1:125–128 (1991); Pober, J. S. et al., *Lab. Invest.* 64:301–305 (1991)). P-selectin and E-selectin bind to a similar spectrum of cells in accordance with the fact that both can bind the SLe$^x$ lectin. The expression of P-selectin is induced by activators such as thrombin, histamine, and hydrogen peroxide.

The expression of E-selectin and P-selectin is reported to reflect inflammatory and hemostatic responses, respectively, to tissue injury (Geng, J. G. et al., *Nature* 343:757–760 (1990); Toothill, V. J. et al., *J. Immunol.* 145:283–291 (1990)). L-selectin has been reported to participate in the recruitment of cells to sites of inflammation (Watson, S. R. et al., *Nature* 349:164–167 (1991); Lewinsohn, D. M. et al., *J. Immunol.* 138:4313–4321 (1987)). All three selectins have been reported to be involved in the recruitment of neutrophils and other leukocytes to sites of inflammation (Arfors, D. E. et al., *Blood* 69:338–340 (1987); Smith, C. W. et al., *J. Clin. Invest.* 82:1746–1756 (1988); Anderson, D. C. et al., *Ann. Rev. Med.* 38:175–194 (1990); Larson, R. S. et al., *Immunol. Rev.* 114:181–217 (1990)).

The selectins have been reported to act by aiding the initial adhesion or "rolling" of neutrophils on activated endothelium (von Andrian, U. H. et al., *Proc. Natl. Acad. Sci.* (*U.S.A.*) 88:7538–7542 (1991); Ley, K. et al., *Blood* 77:2553–2555 (1991); Lawrence, M. B. et al., *Cell* 65:859–873 (1991); Smith, C. W. et al., *J. Clin. Invest.* 83:2008–2017 (1989)). In contrast, molecules of the CD11/CD18 family are thought to mediate the subsequent arrest of the migrating neutrophils, once they have reached a site of inflammation (Anderson, D. C. et al., Ann. Rev. Med. 38:175–194 (1990); Larson, R. S. et al., Immunol. Rev. 114:181–217 (1990); Smith, C. W. et al., *J. Clin. Invest.* 83:2008–2017 (1989); Luscinskas, F. W. et al., *J. Immunol.* 146:1617–1625 (1989)).

Thus, in summary, the ability of leukocytes to maintain the health and viability of an animal requires that they be capable of adhering to other cells (such as endothelial cells). This adherence has been found to require cell-cell contacts which involve specific receptor molecules present on the cell surface of the leukocytes and endothelium. These receptors enable a leukocyte to adhere to other leukocytes or to endothelial, and other non-vascular cells. Humans whose leukocytes lack these cell surface receptor molecules exhibit chronic and recurring infections, as well as other clinical symptoms including defective antibody responses.

Since cellular adhesion is involved in the process through which foreign tissue is identified and rejected, an understanding of this process is of significant value in the fields of inflammation, organ transplantation, tissue grafting, allergy and oncology.

D. OTHER ADHESION MOLECULES

VCAM-1 (vascular cell adhesion molecule - 1) is a cell surface receptor found on vascular cells (Hynes, R. O. *Cell* 48:549–554 (987); Price, G. E., *Science* 246:1303–1306 (1980)). Under normal physiologic conditions, VCAM-1 is either not expressed, or is minimally expressed. It is, however, rapidly induced upon stimulation with TNF-α or IL-1β. VCAM-1 has been shown to bind to the VLA-4 integrin molecule that is expressed on leukocytes and other cells (Springer, T. A., *Nature* 346:425–434 (1990); Hemler, M. E. et al., *Immunol. Rev.* 114:45–65 (1990)). VLA-4 has been shown to mediate lymphocyte binding to endothelium of mucosal lymph nodes (Holtzmann, B. et al. *Cell* 56:37–46 (1989); (Holtzmann, B. et al. *EMBO J.* 8:1735–1741 (1989)), and to mediate cytotoxic T-cell activity (Hemler, M. E. et al., *J. Biol. Chem.* 262:11478–11485 (1987); Hemler, M. E. et al., In: *Leukocyte Adhesion Molecules* (Springer, T. A. et al., eds.) pp44–57, Springer-Verlag, N.Y. (1989)). The expression of VLA-4 is substantially unaffected by cytokines.

II. Production of Transgenic Animals: Microinjection Methods

The most widely used method through which transgenic animals have been produced involves injecting a DNA molecule into the male pronucleus of a fertilized egg (Brinster, R. L. et al., *Cell* 27:223 (1981); Costantini, F. et al., *Nature* 294:92 (1981); Harbers, K. et al., *Nature* 393:540 (1981); Wagner, E. F. et al., *Proc. Natl. Acad. Sci. (U.S.A.)* 78:5016 (1981); Gordon, J. W. et al., *Proc. Natl. Acad. Sci. (U.S.A.)* 73:1260 (1976); Stewart, T. A. et al., *Science* 217:1046–1048 (1982); Palmiter, R. D. et al., *Science* 222:809 (1983); Evans, R. M et al. (U.S. Pat. No. 4,870,009)).

The gene sequence being introduced need not be incorporated into any kind of self-replicating plasmid or virus (Jaenisch, R., *Science*, 240:1468–1474 (1988)). Indeed, the presence of vector DNA has been found, in many cases, to be undesirable (Hammer, R. E. et al., *Science* 235:53 (1987); Chada, K. et al., *Nature* 319:685 (1986); Kollias, G. et al., *Cell* 46:89 (1986); Shani, M., *Molec. Cell. Biol.* 6:2624 (1986); Chada, K. et al., *Nature* 314:377 (1985); Townes, T. et al., *EMBO J.* 4:1715 (1985)).

After being injected into the recipient fertilized egg, the DNA molecules are believed to recombine with one another to form extended head-to-tail concatemers. It has been proposed that such concatemers occur at sites of double-stranded DNA breaks at random sites in the egg's chromosomes, and that the concatemers are inserted and integrated into such sites (Brinster, R. L. et al., *Proc. Natl. Acad. Sci. (U.S.A.)* 82:4438 (1985)). Although it is, thus, possible for the injected DNA molecules to be incorporated at several sites within the chromosomes of the fertilized egg, in most instances, only a single site of insertion is observed (Jaenisch, R., *Science*, 240:1468–1474 (1988)).

Once the DNA molecule has been injected into the fertilized egg cell, the cell is implanted into the uterus of a recipient female, and allowed to develop into an animal. Since all of the animal's cells are derived from the implanted fertilized egg, all of the cells of the resulting animal (including the germ line cells) shall contain the introduced gene sequence. If, as occurs in about 30% of events, the first cellular division occurs before the introduced gene sequence has integrated into the cell's genome, the resulting animal will be a chimeric animal.

By breeding and inbreeding such animals, it has been possible to produce heterozygous and homozygous transgenic animals. Despite any unpredictability in the formation of such transgenic animals, the animals have generally been found to be stable, and to be capable of producing offspring which retain and express the introduced gene sequence.

Since microinjection causes the injected DNA to be incorporated into the genome of the fertilized egg through a process involving the disruption and alteration of the nucleotide sequence in the chromosome of the egg at the insertion site, it has been observed to result in the alteration, disruption, or loss of function of the endogenous egg gene in which the injected DNA is inserted. Moreover, substantial alterations (deletions, duplications, rearrangements, and translocations) of the endogenous egg sequences flanking the inserted DNA have been observed (Mahon, K. A. et al., *Proc. Natl. Acad. Sci. (U.S.A.)* 85:1165 (1988); Covarrubias, Y. et al., *Proc. Natl. Acad. Sci. (U.S.A.)* 83:6020 (1986); Mark, W. et al., *Cold Spr. Harb. Symp. Quant. Biol.* 50:453 (1985)). Indeed, lethal mutations or gross morphological abnormalities have been observed (Jaenisch, R., *Science* 240:1468–1474 (1988); First, N. L. et al., *Amer. Meat Sci. Assn.* 39th Reciprocal Meat Conf. 39:41 (1986)) ).

Significantly, it has been observed that even if the desired gene sequence of the microinjected DNA molecule is one that is naturally found in the recipient egg's genome, integration of the desired gene sequence rarely occurs at the site of the natural gene (Brinster, R. L. et al., *Proc. Natl. Acad. Sci. (U.S.A.)* 86:7087–7091 (1989)). Moreover, introduction of the desired gene sequence does not generally alter the sequence of the originally present egg gene.

Although the site in the fertilized egg's genome into which the injected DNA ultimately integrates cannot be predetermined, it is possible to control the expression of the desired gene sequence such that, in the animal, expression of the sequence will occur in an organ or tissue specific manner (reviewed by Westphal, H., *FASEB J.* 3:117 (1989); Jaenisch, R., *Science* 240:1468–1474 (1988); Meade, H. et al. (U.S. Pat. No. 4,873,316)).

The success rate for producing transgenic animals is greatest in mice. Approximately 25% of fertilized mouse eggs into which DNA has been injected, and which have been implanted in a female, will become transgenic mice. A lower rate has been thus far achieved with rabbits, sheep, cattle, and pigs (Jaenisch, R., *Science* 240:1468–1474 (1988); Hammer, R. E. et al., *J. Animal. Sci.* 63:269 (1986); Hammer, R. E. et al., *Nature* 315:680 (1985); Wagner, T. E. et al., *Theriogenology* 21:29 (1984)). The lower rate may reflect greater familiarity with the mouse as a genetic system, or may reflect the difficulty of visualizing the male pronucleus of the fertilized eggs of many farm animals (Wagner, T. E. et al., *Theriogenology* 21:29 (1984)).

Thus, the production of transgenic animals by microinjection of DNA suffers from at least two major drawbacks. First, it can be accomplished only during the single-cell stage of an animal's life. Second, it requires the disruption of the natural sequence of the DNA, and thus is often mutagenic or teratogenic (Gridley, T. et al., *Trends Genet.* 3:162 (1987)).

III. Production of Chimeric and Transgenic Animals: Recombinant Viral and Retrovital Methods Chimeric and transgenic animals may also be produced using recombinant viral or retroviral techniques in which the gene sequence is introduced into an animal at a multi-cell stage. In such methods, the desired gene sequence is introduced into a virus or retrovirus. Cells which are infected with the virus acquire the introduced gene sequence. If the virus or retrovirus infects every cell of the animal, then the method results in the production of a transgenic animal. If, however, the virus infects only some of the animal's cells, then a chimeric animal is produced.

The general advantage of viral or retroviral methods of producing transgenic animals over those methods which involve the microinjection of non-replicating DNA, is that it is not necessary to perform the genetic manipulations at a single cell stage. Moreover, infection is a highly efficient means for introducing the DNA into a desired cell.

Recombinant retroviral methods for producing chimeric or transgenic animals have the advantage that retroviruses integrate into a host's genome in a precise manner, resulting generally in the presence of only a single integrated retrovirus (although multiple insertions may occur). Rearrangements of the host chromosome at the site of integration are, in general, limited to minor duplications (4–6 base pairs) of host DNA at the host virus junctions (Jaenisch, R., *Science* 240:1468–1474 (1988); see also, Varmus, H., In: *RNA Tumor Viruses* (Weiss, R. et al., Eds.), Cold Spring Harbor Press, Cold Spring Harbor, N.Y., pp. 369–512 (1982)). The method is, however, as mutagenic as microinjection methods.

Chimeric animals have, for example, been produced by incorporating a desired gene sequence into a virus (such as bovine papilloma virus or polyoma) which is capable of infecting the cells of a host animal. Upon infection, the virus can be maintained in an infected cell as an extrachromosomal episome (Elbrecht, A. et al., *Molec. Cell. Biol.* 7:1276 (1987); Lacey, M. et al., *Nature* 322:609 (1986); Leopold, P. et al., *Cell* 51:885 (1987)). Although this method decreases the mutagenic nature of chimeric/transgenic animal formation, it does so by decreasing germ line stability, and increasing oncogenicity.

Pluripotent embryonic stem cells (referred to as "ES" cells) are cells which may be obtained from embryos until the early post-implantation stage of embryogenesis. The cells may be propagated in culture, and are able to differentiate either in vitro or in vivo upon implantation into a mouse as a tumor. ES cells have a normal karyotype (Evans, M. J. et al., *Nature* 291:154–156 (1981); Martin, G. R. et al., *Proc. Natl. Acad. Sci. (U.S.A.)* 78:7634–7638 (1981)).

Upon injection into a blastocyst of a developing embryo, ES cells will proliferate and differentiate, thus resulting in the production of a chimeric animal. ES cells are capable of colonizing both the somatic and germ-line lineages of such a chimeric animal (Robertson, E. et al., *Cold Spring Harb. Conf. Cell Prolif.* 10:647–663 (1983); Bradley A. et al., *Nature* 309:255–256 (1984); Bradley, A. et al., *Curr. Top. Devel. Biol.* 20:357–371 (1986); Wagner, E. F. et al., *Cold Spring Harb. Symp. Quant. Biol.* 50:691–700 (1985); (all of which references are incorporated herein by reference).

In this method, ES cells are cultured in vitro, and infected with a viral or retroviral vector containing the gene sequence of interest. Chimerio animals generated with retroviral vectors have been found to have germ cells which either lack the introduced gene sequence, or contain the introduced sequence but lack the capacity to produce progeny cells capable of expressing the introduced sequence (Evans, M. J. et al., *Cold Spring Harb. Symp. Quant. Biol.* 50:685–689 (1985); Stewart, C. L. et al., *EMBO J.* 4:3701–3709 (1985); Robertson, L. et al., *Nature* (1986); which references are incorporated herein by reference).

Because ES cells may be propagated in vitro, it is possible to manipulate such cells using the techniques of somatic cell genetics. Thus, it is possible to select ES cells which carry mutations (such as in the hprt gene (encoding hypoxanthine phosphoribosyl transferase) (Hooper, M. et al., *Nature* 326:292–295 (1987); Kuehn, M. R. et al., *Nature* 326:295–298 (1987)). Such selected cells can then be used to produce chimeric or transgenic mice which fail to express an active HPRT enzyme, and thus provide animal models for diseases (such as the Lesch-Nyhan syndrome which is characterized by an HPRT deficiency) (Doetschman, T. et al., *Proc. Natl. Acad. Sci. (U.S.A.)* 85:8583–8587 (1988)).

As indicated above, it is possible to generate a transgenic animal from a chimeric animal (whose germ line cells contain the introduced gene sequence) by inbreeding.

The above-described methods permit one to screen for the desired genetic alteration prior to introducing the transfected ES cells into the blastocyst. One drawback of these methods, however, is the inability to control the site or nature of the integration of the vector.

IV. Production of Chimeric and Transgenic Animals: Plasmid Methods

The inherent drawbacks of the above-described methods for producing chimeric and transgenie animals have caused researchers to attempt to identify additional methods through which such animals could be produced.

Gossler, A. et al., for example, have described the use of a plasmid vector which had been modified to contain the gene for neomycin phosphotransferase (nptII gene) to transfect ES cells in culture. The presence of the nptII gene conferred resistance to the antibiotic G418 to ES cells that had been infected by the plasmid (Gossler, A. et al., *Proc. Natl. Acad. Sci. (U.S.A.)* 83:9065–9069 (1986), which reference is incorporated herein by reference). The chimeric animals which received the plasmid and which became resistant to G418, were found to have integrated the vector into their chromosomes.

Takahashi, Y. et al. have described the use of a plasmid to produce chimeric mice cells which expressed an avian crystallin gene (*Development* 102:258–269 (1988), incorporated herein by reference). The avian gene was incorporated into a plasmid which contained the nptII gene. Resulting chimeric animals were found to express the avian gene.

V. Production of Chimeric and Transgenic Animals: Gene Targeting Methods

One approach to producing animals having defined and specific genetic alterations has used homologous recombination to control the site of integration of an introduced marker gene sequence in tumor cells and in fusions between diploid human fibroblast and tetraploid mouse erythroleukemia cells (Smithies, O. et al., *Nature* 317:230–234 (1985)).

This approach was further exploited by Thomas, K. R., and co-workers, who described a general method, known as "gene targeting," for targeting mutations to a preselected, desired gene sequence of an ES cell in order to produce a transgenic animal (Mansour, S. L. et al., *Nature* 336:348–352 (1988); Capecchi, M. R., *Trends Genet.* 5:70–76 (1989); Capecchi, M. R., *Science* 244:1288–1292 (1989); Capecchi, M. R. et al., In: *Current Communications in Molecular Biology,* Capecchi, M. R. (ed.), Cold Spring Harbor Press, Cold Spring Harbor, N.Y. (1989), pp. 45–52; Frohman, M. A. et al., *Cell* 56:145–147 (1989); all of which references are incorporated herein by reference).

It may now be feasible to deliberately alter any gene in a mouse (Capecchi, M. R., *Trends Genet.* 5:70–76 (1989); Frohman, M. A. et al., *Cell* 56:145–147 (1989)). Gene targeting involves the use of standard recombinant DNA techniques to introduce a desired mutation into a cloned DNA sequence of a chosen locus. That mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

Gene targeting has been used to produce chimeric and transgenic mice in which an nptII gene has been inserted into the $\beta_2$-microglobulin locus (Koller, B. H. et al., *Proc. Natl. Acad. Sci. (U.S.A.)* 86:8932–8935 (1989); Zijlstra, M. et al., *Nature* 342:435–438 (1989); Zijlstra, M. et al., *Nature* 344:742–746 (1989); DeChiaba et al., *Nature* 345:78–80

(1990)). Similar experiments have enabled the production of chimeric and transgenic animals having a c-abl gene which has been disrupted by the insertion of an nptII gene (Schwartzberg, P. L. et al., *Science* 246:799–803 (1989)). The technique has been used to produce chimeric mice in which the en-2 gene has been disrupted by the insertion of an nptII gene (Joyner, A. L. et al., *Nature* 338:153–155 (1989)).

Gene targeting has also been used to correct an hprt deficiency in an hprt⁻ ES cell line. Cells corrected of the deficiency were used to produce chimeric animals. Significantly, all of the corrected cells exhibited gross disruption of the regions flanking the hprt locus; all of the cells tested were found to contain at least one copy of the vector used to correct the deficiency, integrated at the hprt locus (Thompson, S. et al., *Cell* 56:313–321 (1989); Koller, B. H. et al., *Proc. Natl. Acad. Sci. (U.S.A.)* 86:8927–8931 (1989)).

In order to utilize the "gene targeting" method, the gene of interest must have been previously cloned, and the intron-exon boundaries determined. The method results in the insertion of a marker gene (i.e. the nptII gene) into a translated region of a particular gene of interest. Thus, use of the gene targeting method results in the gross destruction of the gene of interest.

Recently, chimeric mice carrying the homeobox hox 1.1 allele have been produced using a modification of the gene targeting method (Zimmer, A. et al., *Nature* 338:150–154 (1989). In this modification, the integration of vector sequences was avoided by microinjecting ES cells with linear DNA containing only a portion of the hox 1.1 allele, without any accompanying vector sequences. The DNA was found to cause the gene conversion of the cellular hox allele. Selection was not used to facilitate the recovery of the "converted" ES cells, which were identified using the polymerase chain reaction ("PCR"). Approximately 50% of cells which had been clonally purified from "converted" cells were found to contain the introduced hox 1.1 allele, suggesting to Zimmer, A. et al. either chromosomal instability or contamination of sample. None of the chimeric mice were found to be able to transmit the "converted" gene to their progeny (Zimmer, A. et al., In: *current Communications in Molecular Biology*, Capecchi, M. R. (ed.), Cold Spring Harbor Press, Cold Spring Harbor, N.Y. (1989), pp. 53–58).

Significantly, the use of gene targeting to alter a gene of a cell results in the formation of a gross alteration in the sequence of that gene. The efficiency of gene targeting depends upon a number of variables, and is different from construct to construct. For example, in the CD18 gene constructs used herein, such efficiency was approximately 1/300.

VI. Introduction of Gene Sequences into Somatic Cells

DNA has been introduced into somatic cells to produce variant (chimeric) cell lines. hprt-deficient Chinese hamster ovary (CHO) cells have been transformed with the CHO hprt gene in order to produce a prototrophic cell line (Graf, L. H. et al., *Somat. Cell Genet.* 5:1031–1044 (1979)). Folger et al. examined the fate of a thymidine kinase gene (tk gene) which had been microinjected into the nuclei of cultured mammalian cells. Recipient cells were found to contain from 1 to 100 copies of the introduced gene sequence integrated as concatemers at one or a few sites in the cellular genome (Folger, K. R. et al., *Molec. Cell. Biol.* 2:1372–1387 (1982)). DNA-mediated transformation of an RNA polymerase II gene into Syrian hamster cells has also been reported (Ingles, C. et al., *Molec. Cell. Biol.* 2:666–673 (1982)).

Plasmids conferring host neomycin resistance and guanosine phosphotransferase activity have been transfected into Chinese hamster ovary cells to generate novel cell lines (Robson, C. N. et al., *Mutat. Res.* 163:201–208 (1986)).

VII. Conclusions

The application of the above-described technologies has the potential to produce animals which cannot be produced through classical genetics. For example, animals can be produced which suffer from human diseases (such as AIDS, diabetes, cancer, etc.), and may be valuable in elucidating therapies for such diseases. Chimeric and transgenic animals have substantial use as probes of natural gene expression.

Leder, P. et al. (U.S. Pat. No. 4,736,866) disclose the production of transgenic non-human mammals which contain cells having an exogenously added activated oncogene sequence. Although the animals are disclosed as being useful for assaying for carcinogenic materials, the precise location and structure of the added oncogene sequence in the animals is unknown, and cannot be experimentally controlled. Thus, the value of the animals as a model for oncogenesis is significantly impaired.

Recently, Donehower, L. A. et al. have described the construction of a transgenic mouse that carries a mutation in a chromosomal p53 allele (Donehower, L. A. et al., *Nature* 356:215–221 (1992), herein incorporated by reference). Such an animal is of great importance in studies of tumor suppression and oncogenesis.

Despite the successes of the above-described techniques, the methods have not yet led to the development of a model transgenic animal which can be used to study the conditions responsible for the LAD, or inflammatory responses, in general, and which can be used as a means for developing suitable anti-inflammatory agents and therapies. If however, such animals could be obtained, they would facilitate a better understanding of the inflammatory process; they could be used to assay for the presence of agonists or antagonists of inflammation; they could also be used to identify agents capable of suppressing or preventing cancer, atherosclerosis, transplantation rejection, and autoimmune disease. For example, if mutations which reduce the expression of CD18, CD11a, CD11b, CD11c, VLA-4, ICAM-1, ICAM-2, VCAM-1, P-selectin, E-selectin, or L-selectin, protect an animal against atherosclerosis, transplantation rejection, inflammatory processes, tumor metastasis, or other disease processes, this would be strong evidence that drugs which block the adhesion sites of these proteins would also protect against these disease processes. Thus, chimeric and transgenic animals having altered alleles of these genes would be extremely desirable. The present invention provides such animals, and the methods to produce and use them.

SUMMARY OF THE INVENTION

The present invention provides a desired non-human animal or an animal (including human) cell which contains a predefined, specific and desired alteration in a gene involved in cellular adhesion, which protects the animal from inflammatory disorders. Specifically, the invention pertains to a genetically altered non-human animal (most preferably, a mouse), or a cell (either non-human animal or human) in culture, that is defective in at least one of two alleles of a gene involved in cellular adhesion. The inactivation of at least one of these alleles results in an animal with a reduced inflammatory response which might be beneficial in the case of some disease processes (e.g. atherosclerosis or autoimmune inflammation), and disadvantageous in the case of other processes (e.g. susceptiblity to infectious agents). A genetically altered mouse of this type is able to serve as a useful model for inflammatory disorders. The invention additionally pertains to the use of such non-human animals or animal cells, and their progeny in research and medicine.

In detail, the invention provides a transgenic or chimeric animal cell whose genome comprises two chromosomal alleles of a cellular adhesion gene (such as a CD18, CD11a, CD11b, CD11c, VLA-4, ICAM-1, ICAM-2, VCAM-1, P-selectin, E-selectin, or L-selectin gene), wherein at least one of the two alleles contains a mutation.

The invention also provides a non-human transgenic or chimeric animal having an animal cell whose genome comprises two chromosomal alleles of a cellular adhesion gene, wherein at least one of the two alleles contains a mutation, or a progeny of the animal, or an ancestor of the animal, at an embryonic stage. The animal and the animal cell may be of the same or different species.

The invention also includes the embodiments wherein the cellular adhesion gene encodes CD18, CD11a, CD11b, CD11c, VLA-4, ICAM-1, ICAM-2, VCAM-1, P-selectin, E-selectin, or L-selectin, and in particular, wherein only one of the alleles of the cellular adhesion gene expresses a normal gene product.

The invention also includes the embodiments wherein the animal cell is a human or a non-human animal cell (either germ-line or somatic), and especially wherein the cell is an embryonic stem cell and wherein the cellular adhesion gene is a CD18, CD11a, CD11b, CD11c, VLA-4, ICAM-1, ICAM-2, VCAM-1, P-selectin, E-selectin, or L-selectin gene.

The invention also includes a method for determining the effect of an agent suspected of being capable of affecting a characteristic of an animal cell that is attributable to the presence or expression of a cellular adhesion gene, the method comprising:

A) administering an amount of the agent to a transgenic or chimeric non-human animal cell in cell culture, the cell having a genome that comprises two chromosomal alleles of the cellular adhesion gene, wherein at least one of the two alleles contains a mutation;

B) maintaining the cell culture for a desired period of time after the administration;

C) determining whether a characteristic of the animal cell that is attributable to the presence or expression of the alleles of the cellular adhesion gene has been effected by the administration of the agent.

The invention also includes a method for determining the effect of an agent suspected of being capable of affecting a characteristic of an animal cell that is attributable to the presence or expression of a cellular adhesion gene, the method comprising:

A) administering an amount of the agent to a non-human transgenic or chimeric non-human animal, the animal having a transgenic or chimeric non-human cell whose genome comprises two chromosomal alleles of the cellular adhesion gene, wherein at least one of the two alleles contains a mutation;

B) maintaining the animal for a desired period of time after the administration;

C) determining whether a characteristic of the cell that is attributable to the presence or expression of the alleles of the cellular adhesion gene has been effected by the administration of the agent.

The invention also includes the embodiments of the above method wherein wherein both of the animal's alleles of the cellular adhesion gene have been mutated or wherein only one of the animal's alleles of the cellular adhesion gene has been mutated.

The invention also provides a method of gene therapy comprising altering the genome of a human cell in which at least one chromosomal allele of a cellular adhesion gene contains a mutation, to thereby form a cell wherein the allele expresses a normal cellular adhesion gene product.

BRIEF DESCRIPTION OF THE FIGURES

FIG. 2 shows the vector construct for gene targeting of ICAM-1. The construct is shown above with insertion of a neomycin cassette into an exon of the ICAM-1 gene. The construct can be used as an insertion vector by digestion at the Nhe1 site or can be used as a replacement vector if digestion is performed outside of the region of homology. The genomic DNA is indicated below with a solid box indicating the probe for Southern blotting.

FIG. 4 shows Southern blotting demonstrating germ-line transmission of a mutation in the CD18 gene. DNA is analyzed from a litter of animals born to mice, both of whom are heterozygous for the mutation. Animals 060 and 062 are homozygous normal offspring. Animals 063 and 067 are heterozygous offspring. Animals 061, 064, 065, 066 and 068 are homozygous mutant animals.

DESCRIPTION OF THE PREFERRED EMBODIMENTS

Figure 1:
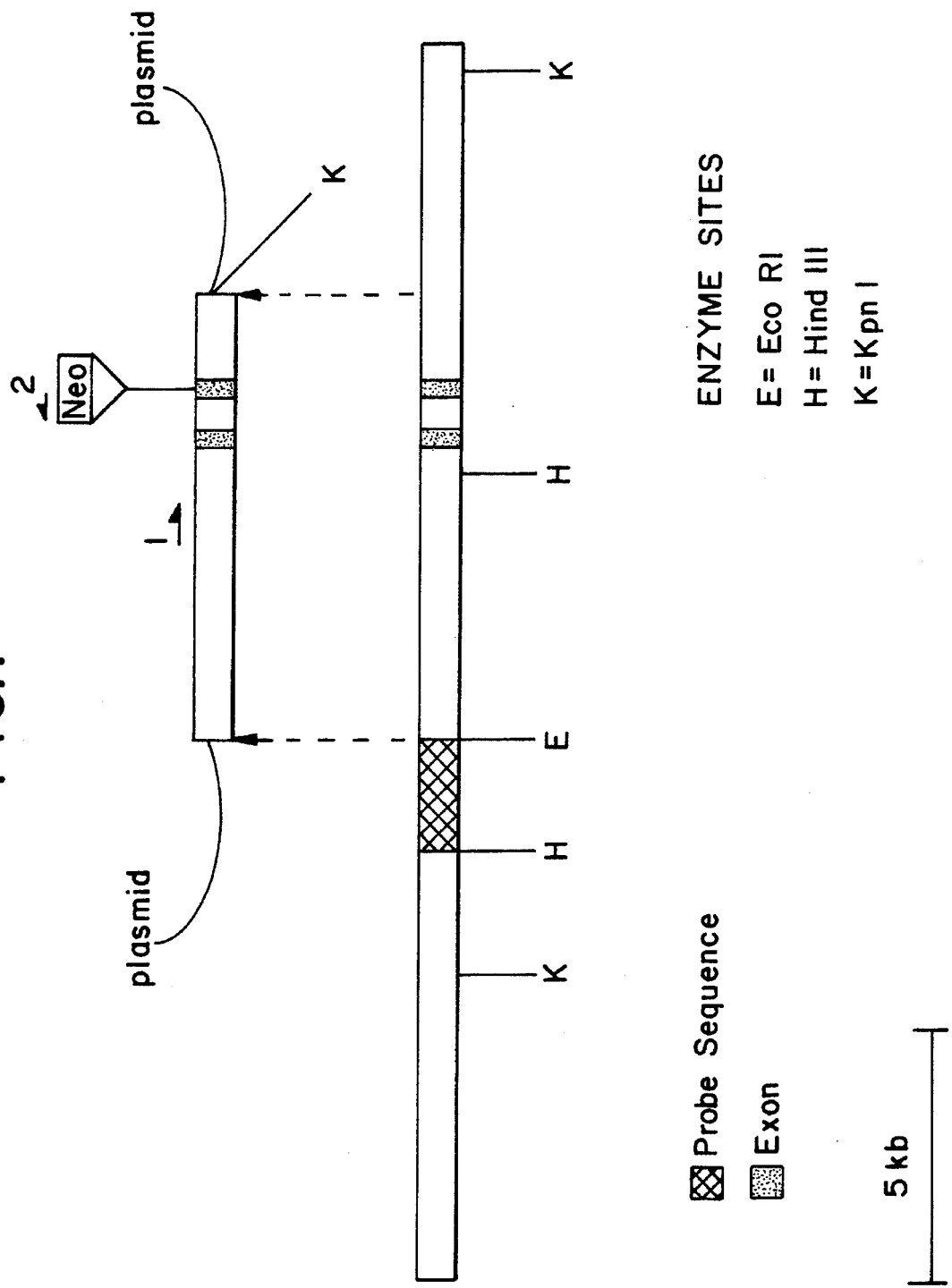
FIG. 1 shows the vector construct for homologous recombination in ES cells for disruption of CD18 gene. The plasmid construct is shown above with insertion of a neomycin cassette in an exon of the CD18 gene. The genomic DNA is shown below with the hatched area representing a probe which was used for Southern blotting. The construct can be linearized at the Kpnl for use as a replacement vector or at the Hindlll for use as an insertion vector.

As discussed above, the capacity of leukocytes to mediate an inflammatory response is dependent upon their ability to migrate to sites of tissue damage. This migration requires the interaction of adhesion molecules of the integrin, super-immunoglobulin and selectin families. As used herein, the term adhesion molecule is defined to encompass the set of molecules: CD18, CD11a, CD11b, CD11c, VLA-4, ICAM-1, ICAM-2, VCAM-1, P-selectin, E-selectin, and L-selectin. The genes that encode these molecules are referred to herein as "cellular adhesion" genes. Genomic clones of CD18, ICAM-1 and P-selectin have been described, and the genomic organization of these genes is known (MacDonald, G. et al., *Genomics* 11:317–323 (1991); Hickstein, D. D. et al., *Proc. Natl. Acad. Sci. (U.S.A.)* 89:2105–2109 (1992); Agura, E. D. et al. *Blood* 79:602–609 (1992); Degitz, K. et al., *J. Biol. Chem.* 266:14024–14030 (1991); Wawryk, S. O. et al. *Int. Immunol.* 3:83–94 (1991); Graf, L. H., Jr. et al., *J. Cell Biol.* 111:160A (1990); Collins, T. et al., *J. Biol. Chem.* 266:2466–2473 (1991); Ord, D. C. et al., *J. Biol. Chem.* 265:7760–7767 (1990), all herein incorporated by reference). Genomic clones of other cellular adhesion genes can be obtained by similar methods.

The present invention relates to the production of non-human transgenic and chimeric animals and cells which contain at least one mutated chromosomal allele of a cellular adhesion gene (and, in a preferred embodiment, one normal allele of that gene so that both heterozygous and homozygous mutant animals can be bred and studied). The present invention encompasses the formation of such cells and non-human animals for any of the cellular adhesion genes. In particular, however, the invention concerns such animals and cells which contain at least one mutated allele of either a CD18, CD11a, CD11b, CD11c, VLA-4, ICAM-1, ICAM-2, VCAM-1, P-selectin, E-selectin, or L-selectin gene.

The animals produced through the use of the present invention are known as either "chimeric" or "transgenic" animals. As the term is used herein, a "chimeric" animal differs from a "transgenic" animal in that in a chimeric animal only some of the animal's cells contain and express the introduced gene sequence, whereas other cells have been unaltered. The capacity of a chimeric animal to transmit the introduced gene sequence to its progeny depends upon whether the introduced gene sequences are present in the germ cells of the animal. Thus, only certain chimeric animals can pass along the desired gene sequence to their progeny. In contrast, all of the cells of a "transgenic" animal contain the introduced gene sequence. Consequently, every transgenic animal is capable of transmitting the introduced gene sequence to its progeny.

As is well known, the cells of humans and animals (especially, rodents (i.e. mouse, rat, hamster, etc.), rabbits, sheep, goats, fish, pigs, cattle and non-human primates) are "diploid" cells, and thus naturally contain two copies ("alleles") of each and every gene of their genome, except for genes that are present on the X chromosome. With respect to genes that are carried on the X chromosome, it is well known that the genomes of the cells of female animals possess two copies of the X chromosome, whereas the genomes of the cells of male animals possess one X chromosome and one Y chromosome. A cell's "genome" consists of all of its heritable DNA (either chromosomal or non-chromosomal (i.e. episomal, viral, etc.)). One of the two alleles of a gene is provided by the animal's or cell's maternal parent; the other set is provided by its paternal parent. The diploid nature of human and animal cells is described by DeRobertis, E. D. P., et al. (*Cell Biology*, 6th Ed., W. B. Saunders Company, Philadelphia, (1975)), and in other similar treatises of cell biology. Where the cells and non-human animals of the present invention contain mutations in both of their chromosomal alleles, such mutations may be the same, or they may be different from one another.

As is well known, an allele may be capable of being expressed by the natural processes operating in a cell. The expression of an allele results in the production of a gene product. The term "allele" as used herein is intended to include any nucleotide sequence that affects the expression of a particular gene. It thus is intended to include any enhancer, promoter, processing, intervening, coding or termination sequence or region of the gene, or any sequence that stabilizes the gene product, or its mRNA, etc.

An allele of a gene is said to be mutated if (1) it is not expressed in a cell or animal, (2) the expression of the allele is altered with respect to the expression of the normal allele of the gene, or (3) the allele expresses a gene product, but that gene product has altered structure, activity, or characteristics relative to the gene product of a normal allele of that gene.

Thus, the terms "mutation" or "mutated" as used herein are intended to denote an alteration in the "normal" or "wild-type" nucleotide sequence of any nucleotide sequence or region of the allele. As used herein, the terms "normal" and "wild-type" are intended to be synonymous, and to denote any nucleotide sequence typically found in nature. The terms "mutated" and "normal" are thus defined relative to one another; where a cell has two chromosomal alleles of a gene that differ in nucleotide sequence, at least one of these alleles is a "mutant" allele as that term is used herein. For example, a "normal CD18 gene product" is the gene product that is expressed by a "normal" CD18 gene. It is well known that different forms of a gene may occur in nature, and these different naturally occurring alleles may result in subtle biological differences. For example, there may be naturally occuring genetic variation in cellular adhesion genes in mouse or human, and these naturally occuring variations may affect inflammatory processes.

A mutation may be "cryptic." A cryptic mutation does not affect either the expression of the mutated gene, or the activity or function of the expressed gene product. Cryptic mutations may be detected through nucleotide sequence analysis. Examples of cryptic mutations include mutations that do not result in a change in the amino acid sequence of the expressed gene product, as well as mutations that result in the substitution of an equivalent amino acid at a particular position in the expressed gene product.

Most preferably, the mutation will be "non-cryptic" and will therefore introduce a change in the nucleotide sequence of the allele that detectably alters either the expression or the activity or function of the allele. A "mutation that detectably alters the expression of an allele," as used herein denotes any change in nucleotide sequence affecting the extent to which the allele is transcribed, processed or translated. Such alterations may be, for example, in an enhancer, promoter, coding or termination region of the allele, mutations which stabilize the gene product, or its mRNA, etc. A "mutation that detectably alters the activity of an allele," as used herein denotes any change in nucleotide sequence that alters the capacity of the expressed gene product to mediate a function of the gene product. Such mutations include changes that diminish or inactivate one or more functions of the expressed product.

Significantly, such mutations also include changes that result in an increase the capacity of the gene product to mediate any function (for example, a catalytic or binding activity, or more relevant to the present invention, an adhesion property) of that gene product. A "mutation that detectably alters the function of an allele," as used herein denotes any change in nucleotide sequence that alters a function of the allele.

Any of a wide variety of methods (treatment with mutagenic compounds, spontaneous isolation, insertional inactivation, site-specific insertions, deletions or substitutions, homologous recombination, etc.) may be used to produce mutations in accordance with the present invention. As indicated above mutations can be readily identified by sequencing, or other means.

An allele is said to be "chromosomal" if the altered DNA is incorporated into the existing chromosomal DNA of the cell. An allele is said to be "extrachomosomal" if the additional DNA is in a form outside of the chromosomes of the cell. As used herein, an allele is said to be "homologous" if its introduction alters or replaces one of the two alleles of a gene in a cell. Conversely, an allele is said to be "nonhomologous" if its introduction results in an increase in the copy number of the total number of alleles of a particular gene which are present in a cell.

The cells that can be produced in accordance with the present invention include both "germ-line" and "somatic" cells. A germ-line cell is a sperm cell or egg cell, or a precursor (i.e. a progenitor) of either; such cells have the potential for transmitting their genome (including the altered cellular adhesion allele) in the formation of progeny animals. A somatic cell is a cell that is not a germ-line cell. Such cells may be "substantially free of naturally occurring contaminants," or may be present in an animal of the same or of different species. A cell is "substantially free of naturally occurring contaminants" when it, or a precursor or ancestor cell, has been purified from tissue (normal, tumor, etc.) in which the cell is, or would be, naturally associated. Two species are said to be the same if they are capable of breeding with one another to produce fertile offspring. Two species are said to be different if they are either incapable of breeding to produce viable offspring, or are substantially incapable of producing fertile offspring.

The term "inflammation," as used herein, is meant to include reactions of either the specific or non-specific defense systems. Many disease processes include simultaneous involvement of both the specific and nonspecific defense systems. As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases, delayed type hypersensitivity response mediated by T-cells (as seen, for example in individuals who test "positive" in the Mantaux test), etc.

A "non-specific defense system reaction" is a response mediated by leukocytes incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: asthma; adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; injury caused by hemodialysis or leukapheresis; ulcerative colitis; Crohn's disease; necrotizing enterocolitis; granulocyte transfusion associated syndromes; and cytokine-induced toxicity.

The present invention is illustrated, in part, through the formation of transgenic or chimeric animals having an altered allele of the CD18. The cDNA sequence of this gene is disclosed by Kishimoto, T. K., et al., *Cell* 48:681–690 (1987), herein incorporated by reference. The sequence of ICAM-1 (Simmons, D. et al., *Nature* 331:624–627 (1988); Staunton, D. E. et al., *Cell* 52:925–933 (1988)); ICAM-2 (Staunton, D. E. et al., *Nature* 339:61–64 (1989)); the CD11 molecules (Sanchez-Madrid, F. et al., *J. Exper. Med.* 158:586–602 (1983); Sanchez-Madrid, F. et al., *J. Exper. Med.* 158:1785–1803 (1983)).); and the selectins (Bevilacqua, M. P. et al., *Science* 243:1160–1165 (1989); Polte, T. et al., *Nucleic Acids Res.* 18:1083 (1989); Tedder, T. F. et al., *J. Exper. Med.* 170:123–133 (1989); Camerini, D. et al., *Nature* 342:78–82 (1989)) is also known. The nature of these molecules is reviewed by Harlan, J. M. et al. (In: *Adhesion Its Role in Inflammatory Disease,* W. H. Freeman and Company, N.Y. (1992), herein incorporated by reference).

I. The Interaction of Mutant and Normal Cellular Adhesion Gene Products

Through the use of site-specific mutagenesis or standard mutational analysis any of a variety of the alleles that encode adhesion molecules can be constructed. In the case of CD18, experience with LAD patients has led to the conclusion that the expression of a single functional CD18 allele is sufficient to confer a relatively normal immune profile to an individual. In contrast, loss of both alleles is associated with significant immune disorder. Thus, by employing animals having one normal allele for an adhesion molecule, and one "null" allele (i.e. an allele, which is either not expressed, or whose expression product has no function), it is possible to study stimuli that are capable of specifically or preferentially inducing mutations in the normal allele. Similarly, by employing animals having one normal allele, and one "hypermorphic" allele (i.e. an allele, which is either expressed at an increased level, or whose expression product has enhanced function), it is possible to study stimuli those domains and residues of the adhesion molecule that are responsible for in vivo activity. Animals having a "hypomorphic" allele (i.e. an allele, which is either expressed at an lowered level, or whose expression product has decreased function) are valuable in studies of the biological significance of the level of gene expression. Such animals are particularly valuable where the total absence of gene expression lead to non-viability. The present invention also permits the production of animals having dominant negative alleles. These are alleles which result in the expression of an abnormal protein that not only has altered activity or function, but also has the capacity to interfere with the function of normal molecules produced by other genes. Examples of such dominant negative alleles include CD18 mutants that are capable of associating with a CD11 molecule, but which are incapable of interacting with ICAM-1; CD18 mutants that acquire the capacity to bind molecules to which normal CD18 cannot bind; ICAM-1 mutants that are capable of binding CD18/CD11, but not human rhinovirus (HRV) (or vice versa); CD18 or CD11 or ICAM mutant molecules that form irreversible CD18/CD11—ICAM complexes; VCAM or selectin mutants that irreversibly bind to their natural ligands, etc.

It would be desirable to produce a transgenic animal whose genome possesses one normal and functional cellular adhesion allele and one non-functional (mutant) allele. Such animals could be used to study the consequences resulting from the loss of one of the two naturally present alleles of a particular cellular adhesion gene, and thus would more clearly aid in elucidating the processes of cellular adhesion. Such animals would also be useful in screening potential inflammatory agonists and antagonists, in developing novel anti-inflammatory therapeutics, and in gene therapy. The present invention provides such an animal.

II. Homologous Recombination

The present invention uses the process of homologous recombination to introduce a specific mutation into the naturally present sequence of an allele of a cellular adhesion gene of an animal cell, most preferably an embryonic stem (ES) cell. The mutated ES cells of non-human animals can then be either cultured in suitable cell culture medium, or introduced into the uterus of a suitable recipient and permitted to develop into a non-human animal. Alternatively, the methods of the present invention may be used to alter the somatic cells of a non-human animal to produce a chimeric non-human animal.

The process of homologous recombination is discussed by Watson, J. D., In: *Molecular Biology of the Gene*, 3rd Ed., W. A. Benjamin, Inc., Menlo Park, Calif. (1977), which reference is incorporated herein by reference. In brief, homologous recombination is a well-studied natural cellular process which results in the scission of two nucleic acid molecules having identical or substantially similar sequences (i.e. "homologous"), and the ligation of the two molecules such that one region of each initially present molecule is now ligated to a region of the other initially present molecule (Sedivy, J. M., *Bio-Technol.* 6:1192–1196 (1988), which reference is incorporated herein by reference).

Homologous recombination is, thus, a sequence specific process by which cells can transfer a "region" of DNA from one DNA molecule to another. As used herein, a "region" of DNA is intended to generally refer to any nucleic acid molecule. The region may be of any length from a single base to a substantial fragment of a chromosome.

For homologous recombination to occur between two DNA molecules, the molecules must possess a "region of homology" with respect to one another. Two DNA molecules possess such a "region of homology" when one contains a region whose sequence is so similar to a region in the second molecule that homologous recombination can occur. Recombination is catalyzed by enzymes which are naturally present in both prokaryotic and eukaryotic cells.

III. Production of Chimeric and Transgenic Animals: Use of Insertion and Replacement Vectors The production of chimeric or transgenic animals having a predetermined mutation in the sequence of at least one of the two alleles of a gene that encodes an adhesion molecule of a human or animal cell a can be accomplished through the use of either replacement or insertion vectors. The use of insertion vectors results in the introduction of vector sequences into the chromosome of the recipient; the use of replacement vectors results in the exchange of a host sequence for that carried by the vector. Replacement vectors may be used to accomplish the deletion of a gene sequence.

Either vector is capable of mutating either a single allele, or both alleles, of the cellular genes that encode an adhesion molecule; it is possible to readily identify such dual mutational events (for example through the use of PCR (Mullis, K. et al., Cold Spring Harbor Symp. Quant. Biol. 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194)), or other methods). Since the frequency of such dual mutational events is the square of the frequency of a single mutational event, cells having mutations in both of alleles of an adhesion molecule will be only a very small proportion of the total population of mutated cells. Thus, the use of classical interbreeding may be preferred in order to obtain homozygous animals.

Figure 3A:
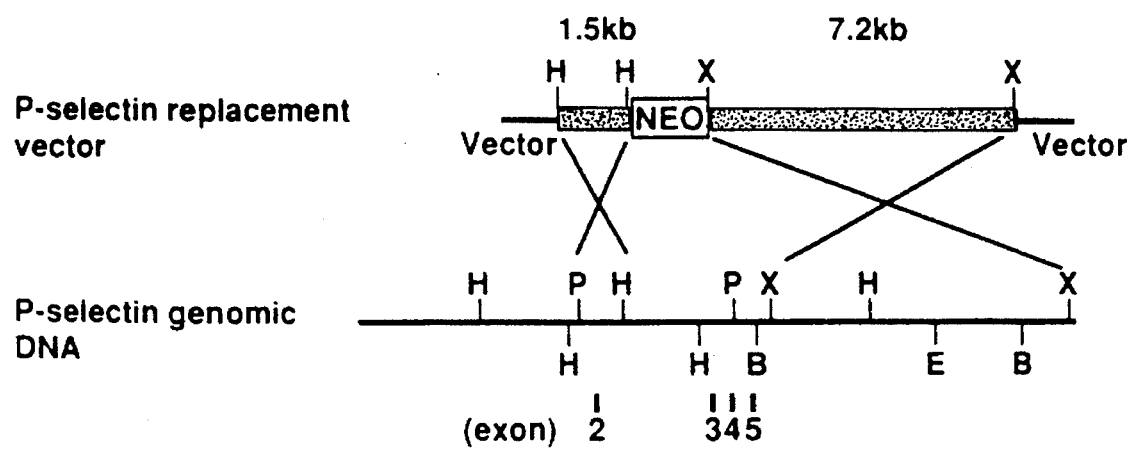
FIG. 3A–B shows the vector construct for gene targeting of the P-selectin gene in mice. The targeting vector, the normal genomic DNA arrangement, and the mutant DNA arrangement are shown. Primers for screening by PCR are indicated as P1 and P2.
Figure 3B:
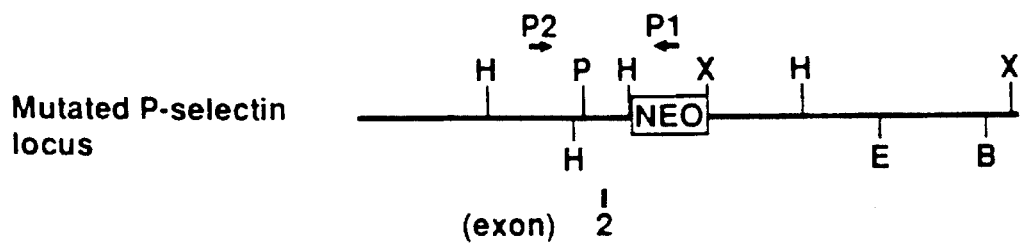

Most preferably, replacement vectors are used to produce the cells and the chimeric or transgenic animals of the present invention. FIG. 1, FIG. 2 and FIG. 3 show the structure of vectors that have been used to alter the CD18 allele, the ICAM-1 allele, or the P-selectin allele of a recipient cell, respectively.

Such vectors will preferably contain a selectable marker gene sequence flanked on at least one side, and preferably on both sides, by a region having homology with the desired allele of an adhesion molecule that is to be altered. A consequence of the use of such a vector is the replacement of the chromosomal allele with the sequence of the selectable marker gene.

Most preferably, the vector molecule(s) which are to be introduced into the recipient cell contains a region of homology with a region of the gene that encodes the adhesion molecule subunit that is to be mutated. In a preferred embodiment, the DNA molecule will contain two regions of homology with the cell's allele of the gene that encodes the adhesion molecule of interest. These regions of homology will preferably flank the precise sequence whose incorporation into the chromosomal allele is desired.

Most preferably, the replacement vector will also contain flanking gene sequences capable of "negative selection" as well as "positive selection," such as the tk gene that encodes thymidine kinase, or the hprt gene that encodes hypoxanthine phosphoribosyl transferase. Cells expressing active thymidine kinase are able to grow in media containing HATG, but are unable to grow in media containing nucleoside analogs such as 5-azacytidine (Giphart-Gassler, M. et al., *Mutat. Res.* 214:223–232 (1989)). Cells containing an active HSV-tk gene are incapable of growing in the presence of gangcylovir or similar agents (Giphart-Gassler, M. et al., *Mutat. Res.* 214:223–232 (1989)). Cells which express an active HPRT enzyme are unable to grow in the presence of certain nucleoside analogs (such as 6-thioguanine, 8-azapurine, etc.), but are able to grow in media supplemented with HAT (hypoxanthine, aminopterin, and thymidine). Conversely, cells which fail to express an active HPRT enzyme are unable to grow in media containing HATG, but are resistant to analogs such as 6-thioguanine, etc. (Littlefield, J. W., *Science* 145:709–710 (1964)). A preferred gene for this purpose is the hprt gene.

In a preferred embodiment, the vector will also contain a selectable marker gene sequence (although, as described below, such sequence can be provided to recipient cells using a second vector or nucleic acid molecule). Examples of such detectable gene sequences include the hprt gene, the tk gene (and especially the tk gene of herpes simplex virus) herein incorporated by reference), the nptII gene (Thomas, K. R. et al., *Cell* 51:503–512 (1987); Mansour, S. L. et al., *Nature* 336:348–352 (1988), both references herein incorporated by reference), or other genes which confer resistance to amino acid or nucleoside analogs, or antibiotics, etc. The detectable marker gene may be any gene which can complement for a recognizable cellular deficiency.

The nptII gene (Southern, P. J., et al., *J. Molec. Appl. Genet.* 1:327–341 (1982); Smithies, O. et al., *Nature*

317:230–234 (1985), which references are incorporated herein by reference) is the most preferred detectable marker gene sequence. Constructs which contain either an NptII gene or an hprt gene and a tk gene are especially preferred.

Replacement (or insertion) vectors are preferably DNA molecule(s) which may be single stranded, but are preferably double stranded. The DNA molecule(s) may be introduced to the cell as one or more RNA molecules which may be converted to DNA by reverse transcriptase or by other means. Preferably, the DNA molecule will be double stranded linear molecule. In the best mode for conducting this embodiment of the invention, such a molecule is obtained by cleaving a closed covalent circular molecule to form a linear molecule. Preferably, a restriction endonuclease capable of cleaving the molecule at a single site to produce either a blunt end or staggered end linear molecule is employed. Most preferably, the nucleotides on each side of this restriction site will comprise at least a portion of the preferred two regions of homology between the DNA molecule being introduced and the gene being mutated (that encodes the adhesion molecule).

Thus, in one method for using a replacement vector, the vector is linearized and introduced into recipient cells (preferably ES cells) as described above. The cells are then cultured in medium that selects for transfectants that have received and integrated the selectable marker gene sequence. The culturing conditions are then altered, such that they now select against recipient cells that have acquired the negative selection gene. In a preferred embodiment of this method, such positive and negative selection is accomplished simultaneously by culturing the cells under conditions that select for the selectable marker gene, but select against the presence of the negative selection gene. Since all of these sequences are present on the same targeting vector molecule, such dual selection requires a recombinational event to occur.

The survivors of such dual selection are then screened either for the function of the chromosomal allele, or more preferably, by Southern blot analysis for clones in which the selectable marker gene sequence has replaced the originally present chromosomal allele.

The invention thus provides a method for altering the natural sequence of a gene that encodes an adhesion molecule through the introduction of a "desired gene sequence" into that gene. The "desired gene sequence" may be of any length, and have any nucleotide sequence. It may comprise one or more gene sequences which encode complete proteins, fragments of such gene sequences, regulatory sequences, etc. Significantly, the desired gene sequence may differ only slightly from a native gene of the recipient cell (for example, it may contain single, or multiple base alterations, insertions or deletions relative to the native gene). The use of such desired gene sequences permits one to create subtle and precise changes in the chromosomal allele of the recipient cell. Thus, the present invention provides a means for manipulating and modulating the expression and regulation of genes that encode adhesion molecules.

In particular, the invention provides a mean for manipulating and modulating the expression and protein structure of genes that encode adhesion molecules through the replacement of a naturally present gene sequence with a "non-selectable" "desired gene sequence." A gene sequence is non-selectable if its presence or expression in a recipient cell provides no survival advantage to the cell under the culturing conditions employed. Thus, by definition, one cannot select for cells which have received a "non-selectable" gene sequence in one of its genes. An example of such a sequence is one that encodes a non-functional allele of gene for an adhesion molecule. In contrast, a "dominant" gene sequence is one which can, under certain circumstances, provide a survival advantage to a recipient cell. The neomycin resistance conferred by the nptII gene is a survival advantage to a cell cultured in the presence of neomycin or G418. The nptII gene is thus a dominant, rather than a non-selectable gene sequence.

In particular, the invention permits the replacement of the naturally present gene sequence of a recipient cell with an "analog" sequence capable of causing the expression of an "analog adhesion molecule." As used herein an "analog adhesion molecule" is a molecule that is capable of binding to the same or to a similar receptor as can be bound by the naturally occurring adhesion molecule.

A sequence is said to be an "analog" of another sequence if the two sequences are substantially similar in sequence, but have minor changes in sequence corresponding to single base substitutions, deletions, or insertions with respect to one another, or if they possess "minor" multiple base alterations.

When the desired gene sequence, flanked by regions of homology with the corresponding gene sequence of the recipient cell, is introduced into the recipient cell as a linear double stranded molecule, whose termini correspond to the regions of homology, a double recombination event with the chromosomal allele of a gene that encodes an adhesion molecule of the cell will occur in approximately 1 out of 225 cells resistant to HAT and FIAU. Such a single recombinational event will lead to the integration of the entire linear molecule into the genome of the recipient cell.

The structure generated by the integration of the linear molecule will undergo a subsequent, second recombinational event (approximately $10^{-5}$–$10^{-7}$ per cell generation). This second recombinational event will result in the elimination of all DNA except for the flanking regions of homology, and the desired DNA sequence from the integrated structure. Thus, the consequence of the second recombinational event is to replace the DNA sequence which is normally present between the flanking regions of homology in the chromosomal allele of the gene for the adhesion molecule, with the desired DNA sequence, and to eliminate the instability of gene replacement.

The DNA molecule containing the desired gene sequence may be introduced into the pluripotent cell by any method which will permit the introduced molecule to undergo recombination at its regions of homology. Some methods, such as direct microinjection, or calcium phosphate transformation, may cause the introduced molecule to form concatemers upon integration. These concatemers may resolve themselves to form non-concatemeric integration structures. Since the presence of concatemers is not desired if the vectors contain coding sequences, methods which produce concatemers are generally not preferred. In a preferred embodiment, the DNA is introduced by electroporation (Toneguzzo, F. et al., *Nucleic Acids Res.* 16:5515–5532 (1988); Quillet, A. et al., *J. Immunol.* 141:17–20 (1988); Machy, P. et al., *Proc. Natl. Acad. Sci. (U.S.A.)* 85:8027–8031 (1988); all of which references are incorporated herein by reference).

After permitting the introduction of the DNA molecule(s), the cells are cultured under conventional conditions, as are known in the art.

In order to facilitate the recovery of those cells which have received the DNA molecule containing the desired gene sequence, it is preferable to introduce the DNA containing the desired gene sequence in combination with a second gene sequence which would contain a detectable marker gene sequence. For the purposes of the present invention, any gene sequence whose presence in a cell permits one to recognize and clonally isolate the cell may be employed as a detectable marker gene sequence.

In one embodiment, the presence of the detectable marker sequence in a recipient cell is recognized by hybridization, by detection of radiolabelled nucleotides, or by other assays of detection which do not require the expression of the detectable marker sequence. Preferably, such sequences are detected using PCR.

A. Use of a Single DNA Molecule Containing Both the Detectable Marker Sequence and the Desired Gene Sequence In a first preferred embodiment, the detectable marker gene sequence, flanked by the regions of homology to the gene that encodes the adhesion molecule, is provided to the recipient cells on the same DNA molecule which contains the desired gene sequence. As discussed previously, it is preferred that this DNA molecule be a linear molecule.

After selection for cells which have incorporated the desired DNA molecule (for example by selection for G418 resistant cells when the detectable marker gene sequence is an expressible nptII gene sequence), the cells are cultured, and the presence of the introduced DNA molecule is confirmed as described above. Approximately $10^7$ cells are cultured and screened for cells which have undergone the second recombinational event (discussed above) resulting in the replacement of a native sequence (i.e. a gene sequence which is normally and naturally present in the recipient cell) with the desired gene sequence.

Any of a variety of methods may be used to identify cells which have undergone the second recombinational event. Direct screening of clones, use of PCR, use of hybridization probes, etc., may all be employed for this purpose. In a preferred embodiment, the DNA molecule will, in addition to the desired gene sequence, the flanking regions of homology and the detectable marker gene sequence, contain an additional gene sequence which will permit the selection or recognition of cells which have undergone the second recombinational event. This additional gene sequence will be excised from the cell's adhesion molecule gene as a direct consequence of the second recombinational event, and can be selected for using a negative selectable marker.

In the first preferred embodiment, the frequency of the second recombinational event is approximately $10^{-5}$. However, the use of a "negative selection" gene sequence permits one to identify such recombinant cells at a frequency of approximately 100%.

The DNA molecule may have a region of heterology located at the proposed insertion site. Insertion of such a vector permits one to select for recombinants which have recombined at the insertion site (and not at other potential sites). If recombination occurs at the desired insertion site, it will lead to the loss of the sequence of heterology located at the proposed insertion site of the DNA molecule (HSVtk, for example). Insertions which result from other recombinational events will retain the sequence of heterology. Thus, by employing a region of heterology which encodes an assayable gene product, or which can be used as a "negative selectable" marker, one can readily determine that the locus of insertion of the recipient cell contains the precise sequence desired. The efficiency of such a vector is approximately 0.5%.

The region of heterology which may be introduced at the insertion site of the DNA molecule may be either short or of substantial size (for example, 2 kb). The site of linearization may be 5', 3' or within the region of heterology. When the site of linearization is within the region of heterology, the efficiency of gene targeting is approximately 2%.

The region of heterology may be located at a site internal to the region of homology where the desired recombination shall occur. Such a construct can be used when one desires to introduce a subtle mutation into a locus of the cellular gene at a site other than that of the site of desired recombination.

B. Use of Different DNA Molecules to Provide the Detectable Marker Sequence and the Desired Gene Sequence In a second preferred embodiment, the detectable marker gene sequence, flanked by the regions of homology, will be provided to the recipient cell on a different DNA molecule from that which contains the desired gene sequence. It is preferred that these molecules be linear molecules.

When provided on separate DNA molecules, the detectable marker gene sequence and the desired gene sequence will most preferably be provided to the recipient cell by co-electroporation, or by other equivalent techniques.

After selection of such recipients (preferably through the use of a detectable marker sequence which expresses the nptII gene and thus confers cellular resistance to the antibiotic G418), the cells are grown up and screened to confirm the insertion event (preferably using PCR).

In the absence of any selection, only one cell in $10^7$ would be expected to have the predicted recombinant structures. If, however, one selects for recipient cells which contain and express a detectable marker sequence (such as the nptII gene), it is possible to obtain a $10^3$ to $10^5$ fold enrichment for cells which have taken up both DNA molecules. Typically, such enrichment enables one to identify the desired recipient cell (in which the introduced DNA has integrated into the cell's genome) by screening only 800–1,500 cells. Such screening is preferably done using PCR, or other equivalent methods. Using such negative selection techniques, one may manipulate the vector copy number.

The two introduced DNA molecules will generally not have integrated into the same site in the genome of the recipient cell. Thus, in some cases, the desired gene sequence will have integrated in a manner so as to replace the native cellular gene sequence between the flanking regions of homology. The locus of integration of the detectable marker gene is unimportant for the purposes of the present invention, provided it is not genetically linked to the locus of the adhesion molecule gene. If desired, however, it is possible to incorporate a gene sequence capable of negative selection along with the DNA containing the detectable marker sequence. Thus, one can ultimately select for cells which have lost the introduced selectable marker gene sequence DNA.

C. Use of Direct Selection to Identify Homologous Recombination Events

Although all of the above-described preferred embodiments enable the isolation of cells in which one of the cell's adhesion molecule alleles has been mutated to contain a desired gene sequence, each embodiment requires the screening of a significant number of candidate cells in order to identify the desired recombinant cell. It is, however, possible to directly select for the desired recombinant cell by employing a variation of the above embodiments.

The method for direct selection of the desired cells relies upon the phenotypic difference in targeted and non-targeted cells and the use of a single gene which can be used for both positive and negative selection.

Typically, in any homologous recombination experiment performed with an insertion vector, three populations of cells will be created. The first class of cells will be those which have failed to receive the desired DNA molecule. This class will comprise virtually all of the candidate cells isolated on completion of the experiment. The second class of cells will be those cells in which the desired gene sequence has been incorporated at a random insertion site (i.e. a site other than in the gene that encodes the adhesion molecule of interest). Approximately one cell in $10^3$–$10^4$ total cells will be in this class. The third class of cells will be those cells in which the desired gene sequence has been incorporated by homologous recombination into a site in the adhesion molecule gene. Approximately one cell in $10^5$–$10^6$ total cells will be in this class.

In the above-described embodiments, the cells of the first class (non-transfected cells) can be eliminated by positive selection, thus necessitating the screening of only about 1,000 cells in order to identify the desired recombinant cell. In the present embodiment, cells of the third class (homologous recombinants) may be selected from the cells of the second class (random insertions) if a phenotypic difference exists between the cells of the two classes.

Since random integration sites are likely to be concatemeric with few single copy clones (depending upon the DNA concentration with which the cells were transfected), such integration events are inherently unstable. Thus, such concatemeric constructs will typically undergo intrachromosomal recombination. Such recombination will always leave one intact copy of the vector in the genome. Thus, all random insertion events may be negatively selected from the population if a negatively selectable marker is included on the vector.

In contrast, cells in which the desired gene sequence has been incorporated into the adhesion molecule gene by homologous recombination will revert with a relatively high frequency (approximately 1 in $10^4$–$10^5$ per cell division depending upon the size of the duplicated structure) to produce a mutated gene that does not contain vector sequences. Therefore, even if the vector contained a negatively selectable gene sequence, such cells will survive negative selection, and can be recovered. The small percentage of homologous recombinant cells which have not undergone reversion will also be eliminated by the negative selection.

A preferred negative selectable marker is the hprt gene (cells expressing an active HPRT enzyme are unable to grow in the presence of certain nucleoside analogues such as 6-thioguanine, etc.). When using 6-thioguanidine as a negative selection agent, a density of $10^7$ cells is preferably used since the efficiency of 6-thioguanidine selection is cell density dependent. A typical experiment with $10^7$ transfected cells would yield approximately 10 revertant cells after successive selection. The relative yield of revertant clones can be substantially increased by using "Poly A Selection" for the first round of selection.

In such a "Poly A Selection" one exploits the fact that, if an introduced DNA molecule were to integrate at random into the host chromosome, it would generally not integrate at a site adjacent to a necessary 3' polyadenylation site. Thus, the mRNA produced by the transcription of such randomly inserted constructs would generally lack polyadenylation. This fact can be exploited by using vectors which permit one to select for a recombinational event that results in integration adjacent to the natural polyadenylation site of the introduced gene sequence (i.e. by homologous recombination rather than by random insertion). As stated above, the frequency of obtaining a desired recombinant cell is approximately $10^{-3}$. By using Poly A Selection, desired cells can be recovered at a frequency of approximately $10^{-2}$. Thus, the poly A selection results in an approximate increase of overall efficiency of nearly 10 fold. Poly A selection may therefore be advantageously used in situations where one desires to minimize or avoid the screening of colonies to identify random versus homologous recombinants.

D. Production of altered alleles containing heterologous sequences

As stated above, the desired gene sequence may be of any length, and have any nucleotide sequence. In particular, it is possible to design the sequence of the desired gene sequence in order to create single, or multiple base alterations, insertions or deletions in any preselected gene of a cell.

For example, if such changes are within a translated region of the gene sequence of the cellular adhesion gene, then a new protein variant of the gene's product can be obtained.

The present invention may be used to produce cells in which the natural allele of a particular adhesion molecule has been replaced with an altered gene sequence, or a heterologous gene. A gene is said to be heterologous to a transgenic cell if it is derivable from a species other than that of the transgenic cell.

In one embodiment, this replacement may be accomplished in a single step. To accomplish such replacement, a DNA molecule containing a desired gene sequence and a region of homology with the gene that encodes the adhesion molecule of interest is introduced into a recipient cell. A selectable marker gene is also introduced into the cell, and used to select for cells which have undergone recombination. The method results in the replacement of the normal sequences adjacent to the region of homology with the heterologous sequences of the desired DNA sequence.

In a second embodiment, this replacement may be accomplished in two steps. As in the embodiment described above, a cell is provided with a DNA molecule containing a desired gene sequence and a region of homology with the gene that encodes the adhesion molecule of interest. The DNA molecule also contains a selectable marker gene used to select for cells which have undergone a recombinational event that has resulted in the insertion of the introduced DNA molecule into their chromosomes at the site of homology.

Significantly, in this embodiment, the introduced DNA molecule will also contain a "negative selectable" marker gene which can be used to select for cells which undergo a second recombinational event that results in the loss of the inserted DNA.

A second DNA molecule is employed to complete the gene replacement. This second DNA molecule need not contain any selectable marker gene. Upon receipt of the second DNA molecule, a second recombinational event occurs which exchanges the "second" DNA molecule for the integrated "first" DNA molecule (including the desired DNA sequence, the selectable marker sequence, and the "negative selectable" marker sequence contained on that molecule).

In another embodiment of the invention, subtle mutations may be introduced into a desired locus using a "cassette" construct containing both a positive selection marker (such as the nptII gene or the gpt gene) and a negative selection marker (such as the tk gene). In this embodiment, one first uses the positive selection capacity of the construct to introduce the two selection markers into a desired locus. One then introduces the desired subtle mutations (substitutions, insertions, deletions, etc.) by providing a cell with a DNA molecule that contains the desired mutation. By selecting for the loss of the "cassette" (using the negative selection marker), one can select for recombinational events which result in the replacement of the "cassette" sequence with the DNA sequence containing the desired mutation.

The present invention may also be used to replace contiguous regions of a chromosome with any desired gene sequence. Thus, the present invention is not limited in the size of the DNA regions which may be altered or replaced. This aspect of the present invention may be considered as a series of 5 steps. The first step in replacing a large region of a chromosome with a desired sequence involves setting up an initial target. In this step, a recipient cell is provided with a DNA molecule which contains a "first fragment" of the total desired replacement sequence. This "first fragment" of the desired replacement sequence contains a selectable marker sequence (most preferably the nptII gene) at its end.

The DNA molecule also contains a "dual selection" gene sequence which encodes a non-functional fragment of a gene sequence for which both a positive and a negative selection exists. An example of such a gene is the gpt gene when used in the context of an hprt⁻ cell. Cells which express a functional gpt gene can be selected for by their ability to grow in HAT medium; Cells which lack a functional gpt gene can be selected for by their ability to grow in the presence of 6-thioguanine.

Homologous recombination results in the insertion of the DNA molecule into the cell's genome at the region of homology. Importantly, since this step results in the creation of a cell whose genome contains the selectable marker gene, it is possible to select for the desired recombinational event.

In the second step of the method, a second DNA molecule is provided to the cell. This second DNA molecule contains a "second fragment" of the desired replacement sequence as well as a sequence of the dual selection gene that, due to an internal deletion, is incapable of encoding a functional gene product. Homologous recombination results in the insertion of the second DNA molecule into the cell's genome in a manner so as to create a functional dual selection gene. Recombination also results in the integration of a non-functional fragment of the dual selection gene. Importantly, since this step results in the creation of a cell whose genome contains a functional dual selection gene, it is possible to select for the desired recombinational event.

In the third step of the method, a third DNA molecule is provided to the cell. This third DNA molecule contains both the "first" and "second" fragments of the desired replacement sequence. Homologous recombination results in the insertion of the third DNA molecule into the cell's genome in a manner so as to delete the functional dual selection gene. The non-functional fragment of the dual selection gene (formed in step 2) is not affected by the recombination, and is retained. Importantly, since this step results in the creation of a cell whose genome lacks the dual selection gene, it is possible to select for the desired recombinational event°

In the fourth step of the method, a fourth DNA molecule is provided to the cell. This fourth DNA molecule contains a "third fragment" of the desired replacement sequence as well as a sequence of the dual selection gene that, as in step 2, is incapable of encoding a functional gene product due to an internal deletion. Homologous recombination results in the insertion of the fourth DNA molecule into the cell's genome in a manner so as to create a functional dual selection gene. Recombination also results in the integration of a non-functional fragment of the dual selection gene. Importantly, since this step results in the creation of a cell whose genome contains a functional dual selection gene, it is possible to select for the desired recombinational event.

In the fifth step of the method, a fifth DNA molecule is provided to the cell. This fifth DNA molecule contains both the "second" and "third" fragments of the desired replacement sequence. Homologous recombination results in the insertion of the fifth DNA molecule into the cell's genome in a manner so as to delete the functional dual selection gene. The non-functional fragment of the dual selection gene (formed in step 4) is not affected by the recombination, and is retained. Importantly, since this step results in the creation of a cell whose genome lacks the dual selection gene, it is possible to select for the desired recombinational event.

As will be appreciated, the net effect of the above-described steps is to produce a cell whose genome has been engineered to contain a "first," "second," and "third" "fragment" of a particular desired gene in a contiguous manner. The steps may be repeated as desired in order to introduce additional "fragments" into the cell's genome. In this manner, cells can be constructed which contain heterologous genes, chromosome fragments, or chromosomes, that could not be introduced using a single vector. As indicated above, it is possible to select for each step of the method.

IV. The Production of Chimeric and Transgenic Animals

The chimeric or transgenic animal cells of the present invention are prepared by introducing one or more DNA molecules into a precursor pluripotent cell, most preferably an ES cell, or equivalent (Robertson, E. J., In: *Current Communications in Molecular Biology*, Capecchi, M. R. (ed.), Cold Spring Harbor Press, Cold Spring Harbor, N.Y. (1989), pp. 39–44, which reference is incorporated herein by reference). The term "precursor" is intended to denote only that the pluripotent cell is a precursor to the desired ("transfected") pluripotent cell which is prepared in accordance with the teachings of the present invention. The pluripotent (precursor or transfected) cell may be cultured in vivo, in a manner known in the art (Evans, M. J. et al,, *Nature* 292:154–156 (1981)) to form a chimeric or transgenic animal.

Any ES cell may be used in accordance with the present invention. It is, however, preferred to use primary isolates of ES cells. Such isolates may be obtained directly from embryos such as the CCE cell line disclosed by Robertson, E. J., In: *Current Communications in Molecular Biology*, Capecchi, M. R. (ed.), Cold Spring Harbor Press, Cold Spring Harbor, N.Y. (1989), pp. 39–44, or from the clonal isolation of ES cells from the CCE cell line (Schwartzberg, P. A. et al., *Science* 246:799–803 (1989), which reference is incorporated herein by reference). Such clonal isolation may be accomplished according to the method of E. J. Robertson (In: *Teratocarcinomas and Embryonic Stem Cells: A Practical Approach,* (E. J. Robertson, Ed.), IRL Press, Oxford, 1987) which reference and method are incorporated herein by reference. The purpose of such clonal propagation is to obtain ES cells which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage. An example of ES cell lines which have been clonally derived from embryos are the ES cell lines, AB1 (hprt⁺) or AB2.1 (hprt⁻).

The ES cells are preferably cultured on stromal cells (such as STO cells (especially SNC4 STO cells) and/or primary embryonic fibroblast cells) as described by E. J. Robertson (In: *Teratocarcinomas and Embryonic Stem Cells: A Practical Approach,* (E. J. Robertson, Ed.), IRL Press, Oxford, 1987, pp 71–112), which reference is incorporated herein by reference. Methods for the production and analysis of chimeric mice are disclosed by Bradley, A. (In: *Teratocarcinomas and Embryonic Stem Cells: A Practical Approach,* (E.

J. Robertson, Ed.), IRL Press, Oxford, 1987, pp 113–151), which reference is incorporated herein by reference. The stromal (and/or fibroblast) cells serve to eliminate the clonal overgrowth of abnormal ES cells. Most preferably, the cells are cultured in the presence of leukocyte inhibitory factor ("lif") (Gough, N. M. et al., *Reprod. Fertil. Dev.* 1:281–288 (1989); Yamamori, Y. et al., *Science* 246:1412–1416 (1989), both of which references are incorporated herein by reference). Since the gene encoding lif has been cloned (Gough, N. M. et al., *Reprod. Fertil. Dev.* 1:281–288 (1989)), it is especially preferred to transform stromal cells with this gene, by means known in the art, and to then culture the ES cells on transformed stromal cells that secrete lif into the culture medium.

ES cell lines may be derived or isolated from any species (for example, chicken, etc.), although cells derived or isolated from mammals such as rodents (i.e. mouse, rat, hamster, etc.), rabbits, sheep, goats, fish, pigs, cattle, primates and humans are preferred.

V. Uses of the Present Invention

The present invention provides human or animal cells which contain a desired gene sequence in one of the two alleles of a cellular adhesion gene of the cell's genome.

In a first embodiment, the invention also provides a means for producing non-human chimeric or transgenic animals whose cells contain such a sequence. The animals which may be produced through application of the described method include chicken, non-human mammals (especially, rodents (i.e. mouse, rat, hamster, etc.), rabbits, sheep, goats, fish, pigs, cattle and non-human primates). Transgenic and chimeric animals may be used to investigate the biological implications of heterozygous and homozygous mutations in a cellular adhesion gene. The animals of the present invention have both diagnostic and therapeutic utility. These animals will be particularly useful in demonstrating whether or not cellular adhesion molecules are important in the pathogenesis of disorders such as atherosclerosis, autoimmune disease, transplantation rejection, or other inflammatory processes.

A. Diagnostic Utility

Since the invention provides a cell, or a transgenic or chimeric non-human animal that contains a single functional allele of a particular cellular adhesion gene, and since such cells will become incapable of participating in cellular adhesion upon the mutation of the functional allele to a non-functional form, the present invention can be used to identify an agent that is capable of affecting a characteristic of an animal cell that is attributable to the presence or expression of a cellular adhesion gene. A characteristic of an animal cell is said to be "attributable to the presence or expression of a cellular adhesion gene," if the characteristic is altered by the absence or lack of expression of that gene. Examples of such characteristics include ability to bind anti-LFA-1 antibody, ability to bind ICAM-1, ability to bind ICAM-2, ability to form heterodimers with a CD11 molecule, etc.

In one embodiment, such agents can increase the capacity of the cells to participate in the adhesion process. Such agents would be expected to exacerbate any undesired inflammatory response. Thus, they would be desirable in studies in which increased, or more rapid induction of transplantation rejection, reperfusion injury of myocardial or other tissues, etc., was desired. Such inflammatory agents are also desirable in the treatment of diseases and conditions in which an enhanced inflammatory response is desirable.

In a second embodiment, such agents can decrease the capacity of the cells to participate in the adhesion process.

Thus, the cells and non-human animals of the present invention have utility in testing potential or suspected anti-inflammatory agents. Moreover, such anti-inflammatory agents can be used in the treatment of diseases and conditions (such as transplantation rejection, reperfusion injury of myocardial or other tissues, etc.) in which an attenuation of the natural inflammatory response may be desired.

One especially preferred cell is a non-human cell which expresses the human cellular adhesion allele(s) on its leukocytes or endothelial cells. Such a cell can be prepared by replacing one of the natural cellular adhesion alleles with their functional human analogs.

Such cells may be used, in accordance with the methods described above to assess the inflammatory or anti-inflammatory potential of agents in cells expressing human cellular adhesion molecules.

In yet another embodiment, by engineering mutant animals that have very different susceptibility to disease precesses (for example, to atherosclerosis or inflammatory disorders) one can identify alleles of the disease that might be found naturally in the human population. Thus, the invention permits the development of prognostic and diagnostic assays (such as isomorphic electrofocusing, restriction fragment length polymorphisms (RFLP) of disease susceptibility, or direct mutation analysis).

1. In Vitro Assays

In one embodiment, one may employ the cells of the present invention, in in vitro cell culture, and incubate such cells in the presence of an amount of the agent whose inflammatory or anti-inflammatory potential is to be measured. This embodiment therefore comprises an in vitro assay of inflammatory activity.

The transformation of the cells to an inflammatory state would be indicative of the inflammatory activity of the assayed agent. Such an inflammatory state may be evidenced by a change in cellular morphology, by enhanced expression of a cellular adhesion molecule, etc.

As is well known in the art, antibodies, or fragments of antibodies, may be used to quantitatively or qualitatively detect the presence of the adhesion molecules on cell surfaces. Since any cell type (i.e. lung, kidney, colon, etc.) may be employed to form the cellular adhesion gene-mutated cells of the present invention, it is possible to determine whether an agent has a tissue specific inflammatory potential. To accomplish this goal, one would incubate a candidate agent in the presence of cellular adhesion gene-mutated cells derived from any of a variety of tissue types. Since cells have tissue-specific antigens, and since antibodies capable of binding to such antigens have been isolated, it is possible to use such antibodies to characterize any tissue-specific antigens which may be expressed by the cellular adhesion gene-mutated cells.

Such detection may be accomplished using any of a variety of immunoassays. For example, by radioactively labeling the antibodies or antibody fragments, it is possible to detect the antigen through the use of radioimmune assays. A good description of a radioimmune assay (RIA) may be found in *Laboratory Techniques and Biochemistry in Molecular Biology*, by Work, T. S., et al., North Holland Publishing Company, N.Y. (1978), with particular reference to the chapter entitled "An Introduction to Radioimmune Assay and Related Techniques" by Chard, T., incorporated by reference herein. Examples of suitable radioisotopic labels include $^3H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}pd$, etc.

Alternatively, enzyme labels, non-radioactive isotopic labels, fluorescent labels, chemiluminescent labels or other suitable labels can be employed.

Examples of suitable enzyme labels include malate dehydrogenase, staphylococcal nuclease, δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, acetylcholine esterase, etc.

Examples of suitable non-radioactive isotopic labels include $^{157}$Gd, $^{55}$Mn, $^{162}$Dy, $^{52}$Tr, $^{56}$Fe, etc.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1–31 (1976)), and Schurs, A. H. W. M., et al. (*Clin. Chim. Acta* 81:1–40 (1977)). coupling techniques mentioned in the latter are the glutaraldehyde method, the periodate method, the dimaleimide method, the m-maleimidobenzyl-N-hydroxy-succinimide ester method, all of which methods are incorporated by reference herein.

The above-described in vitro assay has the advantageous features of low cost, and the capacity to readily screen large numbers of agents. Use of this embodiment facilitates comparisons of test results obtained at different times and conditions. Moreover, because it is possible to use very large numbers of cells in such assays, it is possible to detect inflammatory activity even at very low concentrations. Lastly, since this embodiment can be performed using human cells, it provides a means for determining the inflammatory (or anti-inflammatory) potential of a test compound on human cells.

2. In Vivo Assays

In a second embodiment, one may employ the non-human animals of the present invention, and provide to such animals (by, for example, inhalation, ingestion, injection, implantation, etc.) an amount of the agent whose inflammatory potential is to be measured. The detection of an inflammatory response in such animals would be indicative of inflammatory activity of the assayed agent.

The use of the non-human animals of the present invention is preferred over naturally occurring non-human animals since such natural animals contain two functional cellular adhesion alleles, and thus would require the continued administration of antibodies that are reactive against the product of a cellular adhesion gene in order to mimic the response obtained by the transgenie or chimeric animals of the present invention.

The detection of an inflammatory response in such animals can be accomplished by assaying the animals for the expression of ICAM-1, etc.

Such detection may be accomplished by removing a sample of tissue from a subject and then treating the isolated sample with any suitably labeled antibody (or antibody fragment). Through the use of such a procedure, it is possible to determine not only the presence of antigen, but also the distribution of the antigen on the examined tissue. Using the present invention, those of ordinary skill will readily perceive that any of a wide variety of histological methods can be modified in order to achieve such in situ detection.

The use of an in vivo assay has several advantageous features. The in vivo assay permits one not only to identify inflammatory and anti-inflammatory agents, but also to assess the kind(s) and degree(s) of responses induced by the agent, the number and location (i.e. whether organ or tissue specific) of any elicited response, and the clinical significance of such responses. It further permits an assessment of inflammation which inherently considers the possible natural metabolism of the introduced agent, and the possibility that the introduced agent (or its metabolic by-products) might selectively accumulate in specific tissues or organs of the recipient animal. In short, such an assay provides a true biological model for studying and evaluating the inflammatory potential of an agent in a living non-human animal.

B. Therapeutic Utility

The animals of the present invention have great use in the investigation of human disease processes (and in particular, human inflammatory disease processes) using animal models. In particular, the use of such animals provides an advance over the use of other potential models of inflammation (such as certain breeds of cattle that have a mutation in a cellular adhesion gene).

One advantage of the transgenic animals of the present invention is that they can be engineered to contain any desired, predefined mutation. Moreover, by suitably altering or mutating the promoter region of the gene, the animals can be engineered to express the predefined mutation in a tissue- or time-selective manner, or in response to a desired chemical effector (such as a hormone, pharmaceutical, etc.). A second advantage is that the animals can be bred in large numbers, in order to produce large populations of genetically identical animals at relatively modest cost. In addition to the use of these animals to study inflammation, they may be incorporated into other genetic backgrounds in order to determine the role or relationship of cellular adhesion on the progression of other diseases and conditions. For example, many different types of mice—nude mice, beige mice, scid mice, etc., including some that carry a variety of mutations - are used as recipients for transplanted cells. The effect of the cellular adhesion genes on such mutations in the different types of mice would clarify the role of other genes in inflammatory and other disease processes. Similarly, the invention permits the determination of which cellular adhesion gene(s) are responsible for, or significant in, a particular disease process.

Since the modified cells of the present invention can be introduced into heterologous hosts, the present invention permits the construction of mice (or other animals) that contain human cells. Such mice can provide models for diseases such as AIDS, for which traditional animal models are unavailable or inconvenient. Animals, and in particular mice, having mutations in cellular adhesion genes, alone, or in combination with other animals have great value as recipients for transplantation of cells from heterologous animals (including humans).

The animals of the present invention permit the determination of the relationship between the level of expression of a cellular adhesion gene and the susceptibility of an animal to an inflammatory disease process (such as atherosclerosis, arthritis, autoimmune disease, diabetes mellitus, etc.). The level of expression can be varied by forming homozygous, heterozygous or "compound heterozygous" animals, or by attenuating or driving transcription or translation through the use cellular adhesion alleles having altered regulatory sequences. A compound heterozygous animal contains two dissimilar non-natural alleles of a cellular adhesion gene. A compound heterozygote that contains one severe mutation and one mild mutation provides a means to control the severity of a mutation.

In one embodiment, the mutant and natural animals would be directly compared with one another in order to assess the effect of a mutation in a cellular adhesion gene on an animal's natural susceptibility to disease. Alternatively, the transgenic or chimeric animals of the present invention can be compared with, or derived from animals that have altered genetic backgrounds (such as an animal with enhanced susceptibility to atherosclerosis or autoimmune disease). Since the transgenic or chimeric animals of the present invention are capable of being bred naturally, such diverse genetic backgrounds can be obtained through the conventional breeding of the animals. Alternatively, the animals can be obtained through the mutation of ES cells, and subsequent formation of a novel animal.

Thus, for example, the role of the cellular adhesion process on the formation and metastasis of tumors can be addressed through the isolation of animals having predefined mutations in one or more cellular adhesion genes that additionally carry a mutation in a tumor suppressor gene (such as the p53 gene), an oncogene, etc. Alternatively, the animals can be exposed to conditions that are known or believed to be associated with tumor formation in normal animals.

Significantly, the cells and animals of the present invention can be used to identify agents that decrease the inflammatory potential of the cells or animals. Such agents can be either "prophylactic" or "therapeutic" anti-inflammatory agents. A prophylactic anti-inflammatory agent is a compound that can be provided in advance of any inflammatory response or symptom (for example, prior to, at, or shortly after) the time of an organ or tissue transplant but in advance of any symptoms of organ rejection). The administration of such a compound serves to prevent or attenuate any subsequent inflammatory response (such as, for example, rejection of a transplanted organ or tissue, etc.). In contrast, a "therapeutic" anti-inflammatory agent is a compound that can be provided at (or shortly after) the onset of a symptom of actual inflammation (such as, for example, organ or tissue rejection). The administration of such a compound serves to attenuate any actual inflammation (such as, for example, the actual rejection of a transplanted organ or tissue). Agents that result in a chronic reduction in the expression of a cellular adhesion gene have utility in the treatment of inflammation.

Such anti-inflammatory agents may have general activity (inhibiting all inflammatory responses), or may have a specific activity inhibiting a specific type of response in specific organs and tissue. Thus, the present invention permits the identification of novel anti-inflammatory therapeutics.

The transgenic cells and non-human animals of the present invention can be used to study human gene regulation of a cellular adhesion gene. For example, such cells and animals can be used to investigate the factors regulating CD18 expression.

Significantly, potential anti-inflammatory agents may be found to induce effects in one animal model but not in another animal model. To resolve the potential of such agents, it is often necessary to determine the metabolic patterns in various species, and to then determine the toxicities of the metabolites. The present invention permits one to produce transgenie cells or animals which could facilitate such determinations.

C. Use in Research and in Gene Therapy

The cells and non-human animals of the present invention, quite apart from their uses in veterinary and human medicine, may be used to investigate gene regulation, expression and organization in animals. The methods of the present invention may be used to produce alterations in a regulatory region for the native sequence of a cellular adhesion gene. Thus, the invention provides a means for altering the nature or control of transcription or translation of a cellular adhesion gene, and of altering the gene itself. For example, the invention enables one to introduce mutations which result in increased or decreased gene expression. Similarly, it enables one to impair or enhance the transcriptional capacity of the naturally present allele of the gene in order to decrease or increase its expression. Thus, the present invention permits the manipulation and dissection of cellular adhesion genes.

Such abilities are especially valuable in gene therapy protocols, and in the development of improved animal models of immunosuppression and inflammation.

In one embodiment of the present invention, DNA encoding either a functional cellular adhesion gene, variants of that gene, or other genes which influence the activity of a cellular adhesion gene, may be introduced into the somatic cells of an animal (particularly mammals including humans) in order to provide a treatment for cancer (i.e. "gene therapy"). Most preferably, viral or retroviral vectors are employed for this purpose.

The principles of gene therapy are disclosed by Oldham, R. K. (In: *Principles of Biotherapy*, Raven Press, N.Y., 1987), and similar texts. Disclosures of the methods and uses for gene therapy are provided by Boggs, S. S. (*Int. J, Cell Clon.* 8:80–96 (1990)); Karson, E. M. (*Biol. Reprod.* 42:39–49 (1990)); Ledley, F. D., In: *Biotechnology, A Comprehensive Treatise, volume 7B, Gene Technology*, VCH Publishers, Inc. N.Y., pp 399–458 (1989)); all of which references are incorporated herein by reference.

Although, as indicated above, such gene therapy can be provided to a recipient in order to treat (i.e. suppress, or attenuate) an existing inflammatory response, the principles of the present invention can be used to provide a prophylactic gene therapy to individuals who, due to inherited genetic mutations, or somatic cell mutation, contain cells having impaired expression of a cellular adhesion gene (for example, individuals having only a single functional allele of such a gene, or LAD patients).

Having now generally described the invention, the same will be more readily understood through reference to the following examples which are provided by way of illustration, and are not intended to be limiting of the present invention, unless specified.

EXAMPLE 1

GERM LINE TRANSMISSION OF A TARGETED MUTATION IN THE MURINE CD18 GENE

Inherited defects in the leukocyte adhesion protein CD18 result in marked defects in leukocyte function in human patients. To aid in studying such defects, a retroviral vector capable of transferring expression of the CD18 protein by infection was used to obtain a mouse with a mutation at the CD18 locus.

The murine CD18 cDNA sequence was used as a probe to isolate mouse genomic DNA clones from a τ library. Restriction fragments of one clone that included an exon of the CD18 gene representing base pairs 139–228 of the cDBA sequence were subcloned into the pBluescript vector. The exon was interrupted by ligation of a neomycin resistance cassette into an internal PvuII site. Contiguous restriction fragments were then ligated to reconstruct a plasmid containing approximately 8.9 kb of the mouse gene with the neomycin cassette inserted into a unique PvuII site within the downstream exon. The construct contains a unique HindIII site in the mouse sequence 1 kb upstream of the interrupted exon (FIG. 1). The construct was linearized at this site to create an insertion-type vector.

Pluripotential embryonic stem (ES) cells in tissue culture were transfected by electroporation with the construct linearized at the HindIII site and then selected in the antibiotic G418. Individual G418 resistant ES cell clones were tested for homologous recombination by Southern blot analysis. A flanking genomic probe identified a 20 kb KpnI restriction fragment from wild type ES cell DNA that should be reduced to about 15 kb if the targeted insertion mutation occurred. For 10 of 113 clones tested by Southern analysis, homologous recombination occurred at the CD18 gene as defined by the appearance of the new restriction fragment.

For retroviral expression of CD18, the human cDNA sequence was subcloned into the PAN2 vector and transfected into the retroviral packaging cell lines GPG+E86 (ecotropic) and GP+envAM12 (amphotropic). The expression construct was transferred by retroviral infection using cultured supernatant of the packaging cells. Infection was confirmed by amplification of the construct sequence from infected target cells. Murine cells (bone marrow cells and the cultured cell line P388) expressing endogenous mouse CD11/CD18 protein complexes were shown to express human CD18 protein on their surface after infection with this retroviral vector as determined by immunofluorescent staining. The ability to reconstitute CD18 expression by infection with the CD18 retrovirus permits studies of somatic gene therapy by bone marrow infection of CD18 deficient mice.

As indicated above, lyeukocyte adhesion deficiency (LAD) is an inherited immunodeficiency resulting from mutations in the CD18 gene. To study this immunodeficiency, ES cells containing the targeted CD18 mutation were utilized to produce homozygous mutant transgenic animals. For this purpose, two independent targeted clones were used to generate chimeras. The chimeric mice were then bred in order to obtain germline transmission of the mutation, and and two of the chimeras were found to be capable of passing the targeted genes to their offspring. The transgenic animals were then bred to obtain both heterozygous and homozygous animals. Southern blot analysis of heterozygous and homozygous animals revealed that the insertion resulted in the expected duplication of the 8.9 kb genomic sequence including the vector sequence (FIG. 4).

There is significant evidence of altered biological function in the mutant mice. There is also evidence that this mutation does not completely eliminate gene function. Reverse transcriptase polymerase chain reaction amplification of mRNA from various tissues of homozygous animals demonstrated an absence of normal CD18 mRNA. Immunostaining showed substantial reduction of the CD18 protein on the cell surface of leukocytes from homozygous animals. Homozygous animals were maintained in a pathogen-free environment and showed no signs of illness.

Figure 5:
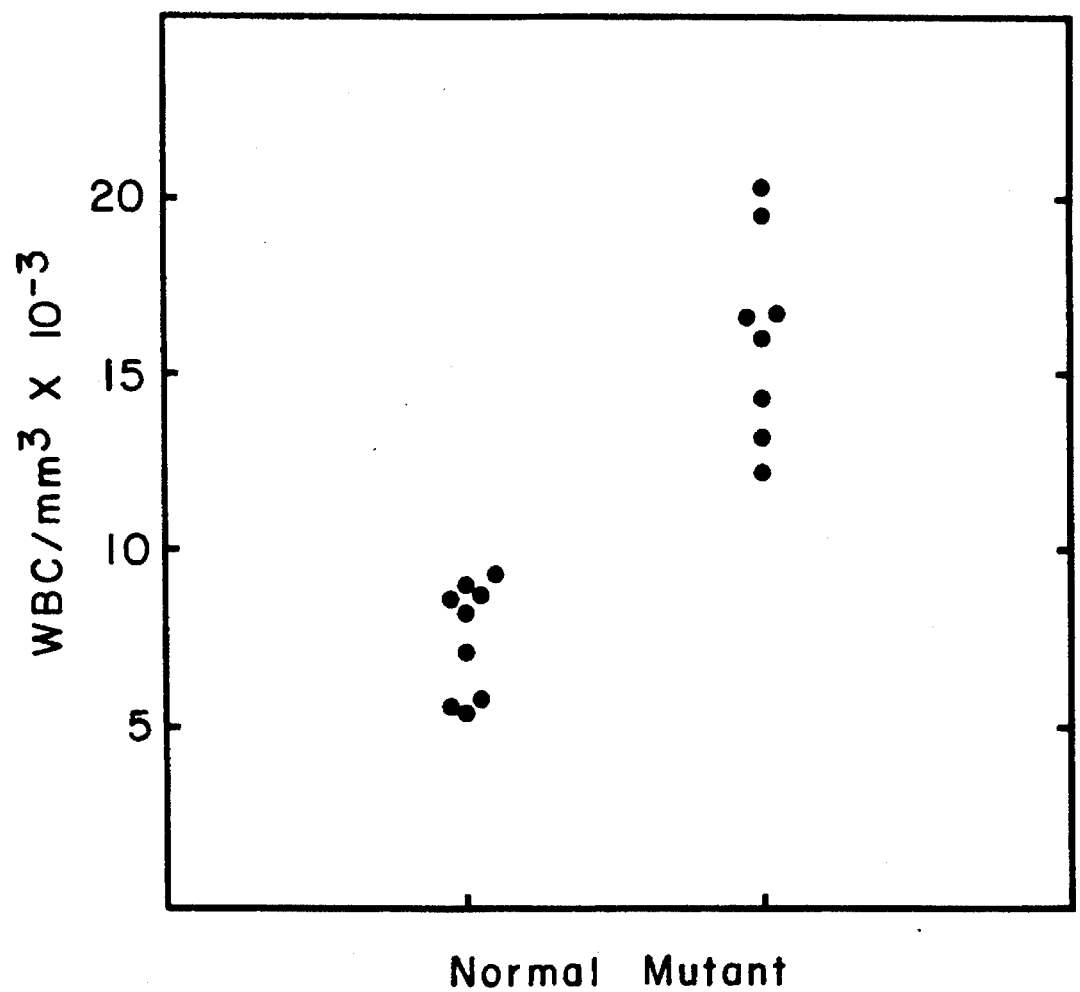
FIG. 5 shows abnormalities of white blood cell count in animals mutant in the CD18 gene. The total white blood cell count of normal and mutant animals is shown indicating a substantial increase in the white blood count of mutant animals. These animals carry a hypomorphic mutation in the CD18 gene.
Figure 6A:
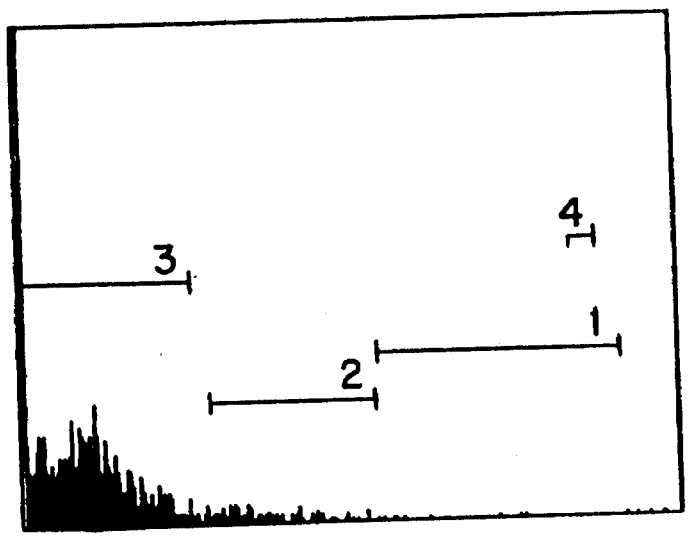
FIG. 6 shows fluorescence activated cell sorting analysis of granulocytes from CD18 mutant mice. Granulocytes from mutant and wild type animals were analyzed using a monoclonal antibody to stain for CD18. Cells were analyzed with and without PMA stimulation. There is a substantial reduction in the CD18 on the surface of granulocytes with or without PMA stimulation.
Figure 6B:
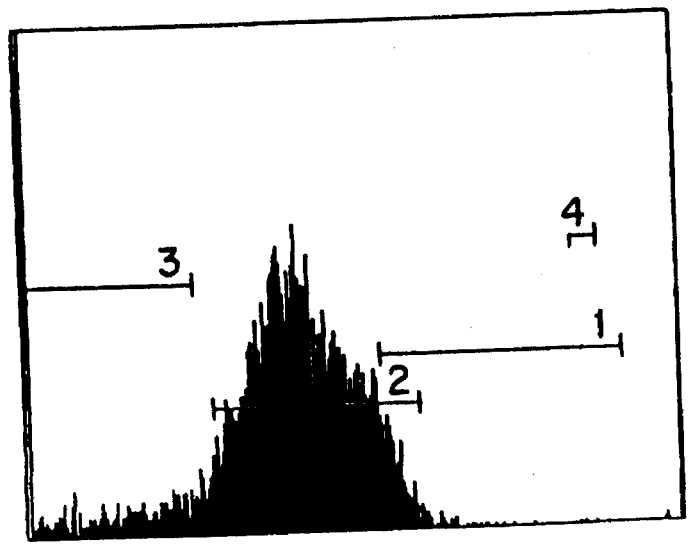
Figure 6C:
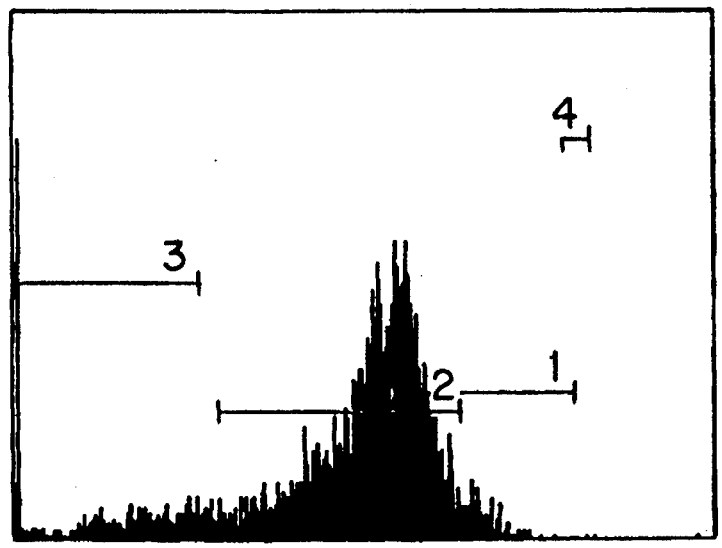
Figure 6D:
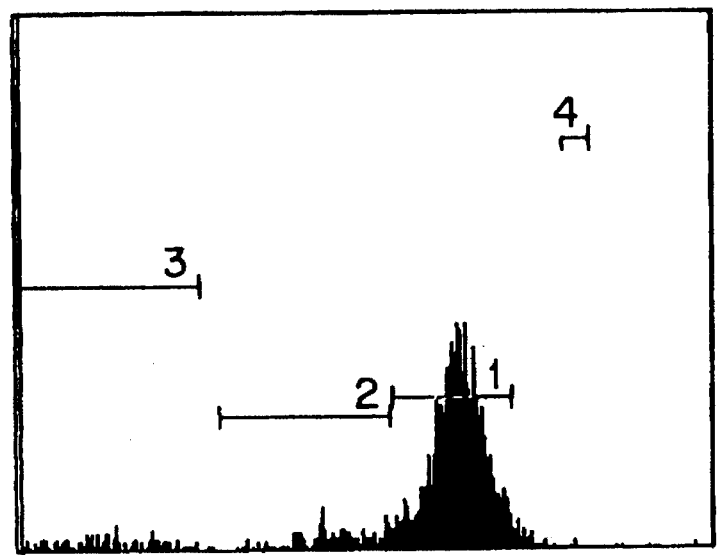

To further characterize the animals, the white cell count was determined for the control and CD18 mutant animals. As shown in FIG. 5, a substantial increase in the white blood count was observed in the CD18 mutant animals that carried a hypomorphic mutation in the CD18 gene.

The granulocytes of mutant and CD18 mutant animals were also evaluated using fluorescence activated cell sorting analysis using a monoclonal antibody to stain for CD18 (FIG. 6). Cells were analyzed with and without PMA stimulation. The mutant animals exhibited a substantial reduction in the CD18 on the surface of granulocytes with or without PMA stimulation.

Figure 7:
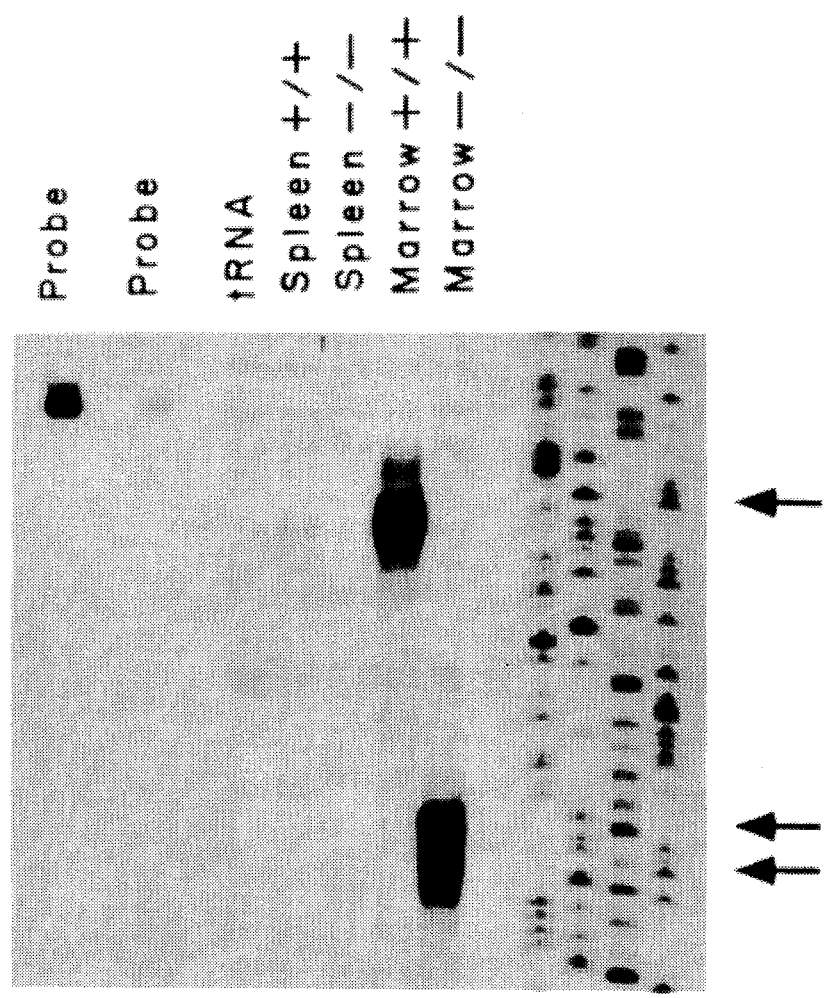
FIG. 7 shows nuclease protection analysis of mRNA from normal and CD18 mutant animals. This figure demonstrates the presence of large amounts of normal mRNA in the bone marrow of normal animals and small amounts of this mRNA in the spleen from normal animals. Mutant animals have no normal mRNA which is detectable and have an abnormal mRNA which is shown by the double arrows.

The nuclease protection analysis of mRNA from normal and CD18 mutant animals was also investigated (FIG. 7). The investigation revealed the presence of large amounts of normal mRNA in the bone marrow of normal animals and small amounts of this mRNA in the spleen from normal animals. Mutant animals had no normal mRNA which was detectable and had an abnormal mRNA.

Transgenic animals having a mutation in their CD18 gene provide a means of probing the relationship between CD18 structure and function. Moreover, the biological properties of the mutant mouse would be expected to be similar to what is observed in humans, dogs, and cattle affected with naturally occurring mutations in this gene. Thus, the fact that the CD18 allele retains function indicates that the methods of the present invention are capable of altering the CD18 allele so as to introduce subtle mutations that do not result in the complete loss of gene function. It thus can be used to explore the critical domains of the CD18 molecule, and to develop hyperactive CD18 variant sequences that would be capable of stimulating a desired inflammatory response. The invention can, however, also be readily used to produce CD18 alleles that completely lack gene function.

Although it may be possible to block CD18 adhesion using monoclonal antibodies, this does not permit the evaluation of the role of the gene over the lifetime of an animal. The animals of the present invention allow for the valuation of the role of the CD18 gene in chronic disease processes. The animals of the present invention may be used in the study of immune suppression, and inflammatory disorders. In particular, such animals are useful in studies of inflammation, atherosclerosis, transplantation rejection, immune disorders, and other disease processes, discussed above, involving inflammatory responses.

EXAMPLE 2

GERM LINE TRANSMISSION OF A TARGETED MUTATION IN THE MURINE ICAM-1 GENE

The invention is further illustrated by the introduction of mutations into the ICAM-1 gene of mice. A 5.5 kb segment of the murine ICAM-1 gene was subcloned into pBluescript and a neomycin resistance gene under the control of the RNA polymerase II promoter was inserted within exon 5 which encodes the fourth extracellular Ig domain (FIG. 2). This mutation is expected to produce a premature stop codon and a truncated protein. This construct was digested with restriction endonucleases to generate either a replacement or an insertion vector. After electroporation into ES cells and 9 days of G418 selection, individual ES cell colonies were picked and screened for homologous recombination by PCR. The screening employed a primer within the neomycin cassette, paired with a primer lying in the ICAM-1 gene, but outside of the region contained in the electroporated plasmids. Using an insertion vector, PCR screening identified 1 in 30 G418 resistant colonies as positive in the homologous recombination event. Numerous chimeric animals were generated by injecting seven different clones with the insertion vector into blastocysts, however, the contribution of the ES cells to the animals was less than 30%.

Figure 8:
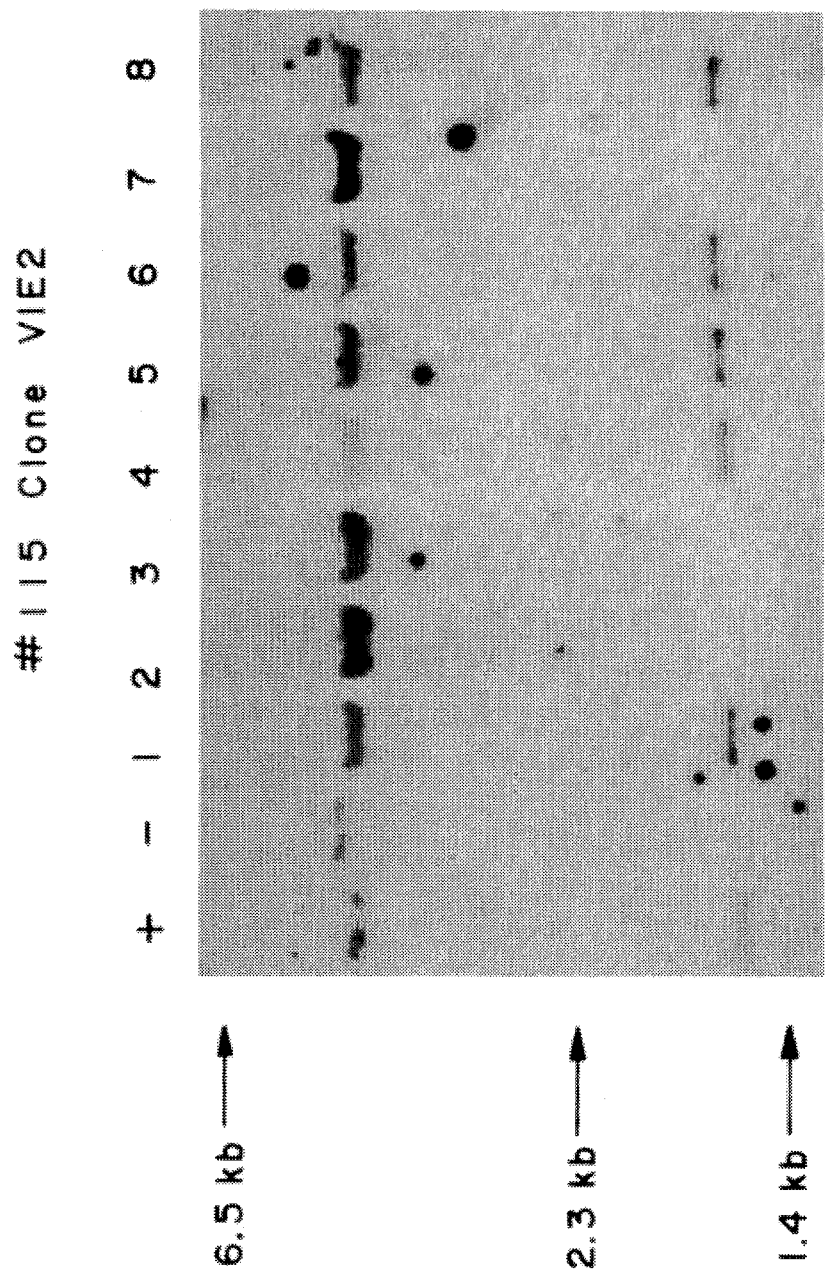
FIG. 8 shows Southern blot demonstrating germ-line transmission of a mutation in the ICAM-1 gene. A series of eight offspring of a chimeric animal were analyzed. The Southern blot fragment showing the presence of the mutation is seen in animals 1, 4, 5, 6 and 8. This demonstrates the heterozygous germ-line transmission of the mutation in the ICAM-1 gene.

Using the same plasmid cut as a replacement vector, several targeted clones were identified at a frequency of 1 in 70. Chimeric animals with extensive ES cell contribution were generated from both AB2.1 (1 of 1) and AB1 (2 of 5) ES cells injected into blastocysts. A series of eight offspring of a chimeric animal were analyzed by Southern blot to demonstrate germ-line transmission of the mutation in the ICAM-1 gene. The Southern blot fragment showing the presence of the mutation was seen in animals 1, 4, 5, 6 and 8 (FIG. 8). The heterozygous progeny of the chimerio animals were mated to produce mice homozygous for the ICAM-1 mutation.

EXAMPLE 3

METHOD FOR THE GERM LINE TRANSMISSION OF A TARGETED MUTATION IN THE MURINE P-SELECTIN GENE

The invention is further illustrated by the introduction of mutations into the P-selectin gene of mice. A construct having a neomycin cassette inserted into an exon of the P-selectin gene is used to form an ICAM-1 mutant animal (FIG. 3). A series of offspring of a chimeric animal are analyzed by Southern blot to demonstrate germline transmission of the mutated gene. Such heterozygous animals are then bred to form homozygous mice.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A transgenic mouse comprising non-naturally occurring alleles of a CD18 gene introduced into its genome via homologous recombination in an embryonic stem cell, wherein said introduction results in the inactivation of the endogenous alleles of said mouse and a reduced capacity of said mouse to mediate cellular adhesion.

2. The mouse of claim 1, wherein said non-naturally occurring alleles are alleles of the human CD18 gene.

3. A method for determining the effect of an agent on a characteristic of a mouse that is attributable to the expression of the CD18 gene, said method comprising:

(A) administering said agent to the mouse of claim 1;

(B) maintaining said mouse for a desired period of time after said administration; and (C) determining whether a characteristic of said mouse that is attributable to the expression of the CD18 gene has been affected by the administration of said agent.

4. The method of claim 3, wherein said non-naturally occurring alleles introduced into said mouse are alleles of the human CD18 gene.

5. The method of claim 3, wherein said agent is suspected of being able to increase an inflammatory response of said mouse.

6. The method of claim 3, wherein said agent is suspected of being able to decrease an inflammatory response of said mouse.

7. A transgenic mouse comprising non-naturally occurring alleles of a ICAM-1 gene introduced into its genome via homologous recombination in an embryonic stem cell, wherein said introduction results in the inactivation of the endogenous alleles of said mouse and a reduced capacity of said mouse to mediate cellular adhesion.

8. The mouse of claim 7, wherein said non-naturally occurring alleles are alleles of the human ICAM-1 gene.

9. A method for determining the effect of an agent on a characteristic of a mouse that is attributable to the expression of the ICAM-1 gene, said method comprising:

(A) administering said agent to the mouse of claim 7;

(B) maintaining said mouse for a desired period of time after said administration; and (C) determining whether a characteristic of said mouse that is attributable to the expression of the ICAM-1 gene has been affected by the administration of said agent.

10. The method of claim 9, wherein said non-naturally occurring alleles introduced into said mouse are alleles of the human ICAM-1 gene.

11. The method of claim 9, wherein said agent is suspected of being able to increase an inflammatory response of said mouse.

12. The method of claim 9, wherein said agent is suspected of being able to decrease an inflammatory response of said mouse.

* * * * *